US008658163B2

(12) United States Patent
Fallon

(10) Patent No.: US 8,658,163 B2
(45) Date of Patent: Feb. 25, 2014

(54) COMPOSITIONS AND USE THEREOF FOR TREATING SYMPTOMS OF PREECLAMPSIA

(75) Inventor: Joan M. Fallon, Yonkers, NY (US)

(73) Assignee: Curemark LLC, Rye, NY (US)

( * ) Notice: Subject to any disclaimer, the term of this patent is extended or adjusted under 35 U.S.C. 154(b) by 1488 days.

(21) Appl. No.: 12/047,818

(22) Filed: Mar. 13, 2008

(65) Prior Publication Data

US 2009/0232789 A1  Sep. 17, 2009

(51) Int. Cl.
*A61K 38/48* (2006.01)

(52) U.S. Cl.
USPC .................. 424/94.63; 424/94.1; 424/94.6

(58) Field of Classification Search
None
See application file for complete search history.

(56) References Cited

U.S. PATENT DOCUMENTS

| | | | |
|---|---|---|---|
| 3,002,883 A | 10/1961 | Butt et al. |
| 3,223,594 A | 12/1965 | Serge |
| 3,357,894 A | 12/1967 | Jose et al. |
| 3,515,642 A | 6/1970 | Mima et al. |
| 3,574,819 A | 4/1971 | Gross et al. |
| 3,860,708 A | 1/1975 | Prout |
| 3,940,478 A | 2/1976 | Kurtz |
| 4,079,125 A * | 3/1978 | Sipos ............................ 424/480 |
| 4,145,410 A | 3/1979 | Sears |
| 4,241,046 A | 12/1980 | Papahadjopoulos et al. |
| 4,826,679 A | 5/1989 | Roy |
| 5,190,775 A | 3/1993 | Klose |
| 5,250,418 A | 10/1993 | Moller et al. |
| 5,324,514 A | 6/1994 | Sipos |
| 5,378,462 A | 1/1995 | Boedecker et al. |
| 5,436,319 A | 7/1995 | Kung et al. |
| 5,437,319 A | 8/1995 | Garuglieri |
| 5,439,935 A | 8/1995 | Rawlings et al. |
| 5,460,812 A | 10/1995 | Sipos |
| 5,476,661 A | 12/1995 | Pillai et al. |
| 5,527,678 A | 6/1996 | Blaser et al. |
| 5,585,115 A | 12/1996 | Sherwood et al. |
| 5,607,863 A | 3/1997 | Chandler |
| 5,648,335 A | 7/1997 | Lewis et al. |
| 5,674,532 A | 10/1997 | Atzl et al. |
| 5,686,311 A | 11/1997 | Shaw |
| 5,750,104 A * | 5/1998 | Sipos ......................... 424/94.21 |
| 5,776,917 A | 7/1998 | Blank et al. |
| 5,858,758 A | 1/1999 | Hillman et al. |
| 5,952,178 A | 9/1999 | Lapidus et al. |
| 5,958,875 A | 9/1999 | Longo et al. |
| 5,977,175 A | 11/1999 | Lin |
| 5,985,891 A | 11/1999 | Rowe |
| 6,011,001 A | 1/2000 | Navia et al. |
| 6,013,286 A | 1/2000 | Klose |
| 6,020,310 A | 2/2000 | Beck et al. |
| 6,020,314 A | 2/2000 | McMichael |
| 6,096,338 A | 8/2000 | Lacy et al. |
| 6,149,585 A | 11/2000 | Gray |
| 6,153,236 A | 11/2000 | Wu et al. |
| 6,168,569 B1 | 1/2001 | McEwen et al. |
| 6,187,309 B1 | 2/2001 | McMichael et al. |
| 6,197,746 B1 | 3/2001 | Beck et al. |
| 6,210,950 B1 | 4/2001 | Johnson et al. |
| 6,251,478 B1 | 6/2001 | Pacifico et al. |
| 6,261,602 B1 | 7/2001 | Calanchi et al. |
| 6,261,613 B1 | 7/2001 | Narayanaswamy et al. |
| 6,280,726 B1 | 8/2001 | Weinrauch et al. |
| 6,287,585 B1 | 9/2001 | Johansen |
| 6,309,669 B1 | 10/2001 | Setterstrom et al. |
| 6,399,101 B1 | 6/2002 | Frontanes et al. |
| 6,482,839 B1 | 11/2002 | Thornfeldt |
| 6,498,143 B1 | 12/2002 | Beck et al. |
| 6,534,063 B1 | 3/2003 | Fallon |
| 6,534,259 B1 | 3/2003 | Wakefield |
| 6,569,463 B2 | 5/2003 | Patel et al. |
| 6,632,429 B1 | 10/2003 | Fallon |
| 6,660,831 B2 | 12/2003 | Fallon |
| 6,727,073 B1 | 4/2004 | Moore et al. |
| 6,743,447 B2 | 6/2004 | Labergerie et al. |
| 6,764,447 B2 | 7/2004 | Iliff |
| 6,783,757 B2 | 8/2004 | Brudnak |
| 6,790,825 B2 | 9/2004 | Beck et al. |
| 6,797,291 B2 | 9/2004 | Richardson |
| 6,808,708 B2 | 10/2004 | Houston |
| 6,821,514 B2 | 11/2004 | Houston |
| 6,835,397 B2 | 12/2004 | Lee et al. |

(Continued)

FOREIGN PATENT DOCUMENTS

| | | |
|---|---|---|
| CN | 1031562 A | 3/1989 |
| DE | 4332985 | 3/1995 |

(Continued)

OTHER PUBLICATIONS

Rajakumar et al., Placenta, vol. 29, pp. 290-299, 2008.*
U.S. Appl. No. 13/002,136, filed Dec. 30, 2010, Fallon.
Adams. "Summary of Defeat Autism Now! (DNN!) Oct. 2001 Conference," retrieved from the internet Dec. 18, 2008. http://puterakembara.org/rm/DAN2001.htm.
Advisory Action dated Jun. 3, 2008 for U.S. Appl. No. 10/681,018.
Amendment and Response dated Apr. 7, 2010 in Reply to Restriction Requirement dated Oct. 7, 2009 for U.S. Appl. No. 12/283,090.
Amendment and Response dated Jun. 30, 2010 to Restriction Requirement dated Jan. 13, 2010 for U.S. Appl. No. 12/487,868.

(Continued)

*Primary Examiner* — Hope Robinson
(74) *Attorney, Agent, or Firm* — Wilson Sonsini Goodrich & Rosati

(57) ABSTRACT

A therapeutic agent for the treatment of toxemia, preeclampsia and eclampsia and a method for preparing the therapeutic agent is disclosed. The therapeutic agent is a stable pharmaceutical preparation containing, but not limited to, digestive/pancreatic enzymes. The therapeutic agent may be manufactured by a variety of encapsulation technologies. Delivery of the therapeutic agent may be made orally, through injection, by adherence of a medicated patch or by other methods. Further, a method of using the presence of chymotrypsin in the maternal GI tract as a biomarker to determine the likelihood of developing preeclampsia, a pregnancy induced hypertension, and eclampsia/toxemia is disclosed.

12 Claims, 4 Drawing Sheets

(56) References Cited

U.S. PATENT DOCUMENTS

| | | | |
|---|---|---|---|
| 6,852,487 B1 | 2/2005 | Barany et al. |
| 6,899,876 B2 | 5/2005 | Houston |
| 6,923,988 B2 | 8/2005 | Patel et al. |
| 7,091,182 B2 | 8/2006 | Beck et al. |
| 7,101,573 B2 | 9/2006 | Szymczak et al. |
| 7,122,357 B2 | 10/2006 | Sander et al. |
| 7,129,053 B1 | 10/2006 | Reiter et al. |
| 7,138,123 B2 | 11/2006 | Fallon |
| 7,232,670 B2 | 6/2007 | D'Azzo et al. |
| 7,381,698 B2 | 6/2008 | Fein et al. |
| 7,395,216 B2 | 7/2008 | Rosenfeld et al. |
| 7,479,378 B2 | 1/2009 | Potthoff et al. |
| 7,483,747 B2 | 1/2009 | Gliner et al. |
| 7,588,757 B2 | 9/2009 | Ozawa et al. |
| 7,630,913 B2 | 12/2009 | Kay |
| 7,658,918 B1 | 2/2010 | Ortenzi et al. |
| 7,945,451 B2 | 5/2011 | Cosentino et al. |
| 8,055,516 B2 | 11/2011 | Iliff |
| 8,066,636 B2 | 11/2011 | Iliff |
| 2002/0037284 A1 | 3/2002 | Fallon |
| 2002/0081628 A1 | 6/2002 | Fallon |
| 2002/0090653 A1 | 7/2002 | Fallon |
| 2003/0097122 A1 | 5/2003 | Ganz et al. |
| 2004/0005304 A1 | 1/2004 | Brudnak |
| 2004/0028689 A1 | 2/2004 | Borody |
| 2004/0029752 A1 | 2/2004 | Sava et al. |
| 2004/0057944 A1 | 3/2004 | Galle et al. |
| 2004/0057962 A1 | 3/2004 | Timmerman |
| 2004/0071683 A1 | 4/2004 | Fallon |
| 2004/0076590 A1 | 4/2004 | Wilkins |
| 2004/0101562 A1 | 5/2004 | Maio |
| 2004/0121002 A1 | 6/2004 | Lee et al. |
| 2004/0209790 A1 | 10/2004 | Sava et al. |
| 2005/0170479 A1* | 8/2005 | Weaver et al. ............... 435/134 |
| 2005/0187130 A1 | 8/2005 | Brooker et al. |
| 2006/0105379 A1 | 5/2006 | Wu et al. |
| 2006/0115467 A1 | 6/2006 | Pangborn et al. |
| 2006/0182728 A1 | 8/2006 | Fallon |
| 2006/0183180 A1 | 8/2006 | Fallon |
| 2006/0198838 A1 | 9/2006 | Fallon |
| 2006/0258599 A1 | 11/2006 | Childers |
| 2006/0259995 A1 | 11/2006 | Cayouette et al. |
| 2007/0031399 A1 | 2/2007 | Edens et al. |
| 2007/0053895 A1 | 3/2007 | Fallon |
| 2007/0092501 A1 | 4/2007 | Houston |
| 2007/0116695 A1 | 5/2007 | Fallon |
| 2007/0148151 A1 | 6/2007 | Frink et al. |
| 2007/0148152 A1 | 6/2007 | Shlieout et al. |
| 2007/0148153 A1 | 6/2007 | Shlieout et al. |
| 2008/0019959 A1 | 1/2008 | Becher et al. |
| 2008/0020036 A1 | 1/2008 | Jolly |
| 2008/0058282 A1 | 3/2008 | Fallon |
| 2008/0112944 A1 | 5/2008 | Pangborn et al. |
| 2008/0152637 A1 | 6/2008 | Fallon |
| 2008/0161265 A1 | 7/2008 | Fallon et al. |
| 2008/0166334 A1 | 7/2008 | Fallon |
| 2008/0219966 A1 | 9/2008 | Fallon |
| 2008/0254009 A1 | 10/2008 | Finegold |
| 2008/0274174 A1 | 11/2008 | Ortenzi et al. |
| 2008/0279839 A1 | 11/2008 | Schuler et al. |
| 2008/0279953 A1 | 11/2008 | Ortenzi et al. |
| 2008/0317731 A1 | 12/2008 | Gramatikova et al. |
| 2009/0117180 A1 | 5/2009 | Ortenzi et al. |
| 2009/0130081 A1 | 5/2009 | Fallon |
| 2009/0197289 A1 | 8/2009 | Fallon |
| 2009/0226414 A1 | 9/2009 | Tijssen et al. |
| 2009/0233344 A1 | 9/2009 | Kurfurst et al. |
| 2009/0263372 A1 | 10/2009 | Fallon |
| 2009/0285790 A1 | 11/2009 | Fallon |
| 2009/0286270 A1 | 11/2009 | Fallon |
| 2009/0304670 A1 | 12/2009 | Edens et al. |
| 2009/0324572 A1 | 12/2009 | Fallon |
| 2009/0324730 A1 | 12/2009 | Fallon |
| 2010/0092447 A1 | 4/2010 | Fallon |
| 2010/0169409 A1 | 7/2010 | Fallon et al. |
| 2010/0196344 A1 | 8/2010 | Margolin et al. |
| 2010/0209507 A1 | 8/2010 | Lin et al. |
| 2010/0233218 A1 | 9/2010 | Fallon |
| 2010/0239559 A1 | 9/2010 | Freedman et al. |
| 2010/0260857 A1 | 10/2010 | Fallon et al. |
| 2010/0270183 A1 | 10/2010 | Ortenzi et al. |
| 2011/0052706 A1 | 3/2011 | Moest et al. |
| 2011/0081320 A1 | 4/2011 | Westall et al. |
| 2012/0070504 A1 | 3/2012 | Fallon |
| 2012/0258149 A1 | 10/2012 | Fallon et al. |

FOREIGN PATENT DOCUMENTS

| | | |
|---|---|---|
| EP | 0451484 A1 | 10/1991 |
| EP | 0564739 A2 | 10/1993 |
| EP | 0564739 A3 | 4/1995 |
| EP | 1162995 B1 | 6/2003 |
| EP | 1335706 B1 | 4/2005 |
| GB | 2347742 A | 9/2000 |
| JP | 62230714 A | 10/1987 |
| WO | WO 95/22344 A1 | 8/1995 |
| WO | WO 98/22499 A2 | 5/1998 |
| WO | WO 98/22499 A3 | 7/1998 |
| WO | WO 98/52593 A1 | 11/1998 |
| WO | WO 99/64059 A2 | 12/1999 |
| WO | WO 00/09142 A1 | 2/2000 |
| WO | WO 99/64059 A3 | 3/2000 |
| WO | WO 01/27612 A2 | 4/2001 |
| WO | WO 01/43764 A2 | 6/2001 |
| WO | WO 01/27612 A3 | 10/2001 |
| WO | WO 01/43764 A3 | 11/2001 |
| WO | WO 02/14537 A2 | 2/2002 |
| WO | WO 02/14537 A3 | 5/2002 |
| WO | WO 2006/044529 A1 | 4/2006 |
| WO | WO 2007/147714 A1 | 12/2007 |
| WO | WO 2009/114757 A2 | 9/2009 |
| WO | WO 2010/002972 A1 | 1/2010 |
| WO | WO 2010/025126 A1 | 3/2010 |
| WO | WO 2010/080830 A1 | 7/2010 |
| WO | WO 2010/080835 A1 | 7/2010 |
| WO | WO 2011/000924 A1 | 1/2011 |

OTHER PUBLICATIONS

Amendment dated Oct. 20, 2008 in Reply to Notice Non-responsive Amendment dated Sep. 22, 2008 for U.S. Appl. No. 11/232,180.
Amendment dated Oct. 24, 2008 in Reply to Notice of Non-Responsive Amendment dated Sep. 25, 2008 for U.S. Appl. No. 11/555,697.
Amendment dated Oct. 28, 2009 in Reply to Final Office Action dated Apr. 28, 2009 for U.S. Appl. No. 10/681,018.
Amendment dated Nov. 13, 2009 in Reply to Final Office Action dated Jul. 27, 2004 for U.S. Appl. No. 09/990,909.
Amendment dated Nov. 17, 2007 in Reply to Restriction Requirement dated Oct. 17, 2007 for U.S. Appl. No. 11/555,697.
Amendment dated Dec. 12, 2007 in Reply to Office Action dated Aug. 8, 2007 for U.S. Appl. No. 11/213,382.
Amendment dated Dec. 7, 2007 in Reply to Office Action dated Aug. 7, 2007 for U.S. Appl. No. 10/681,018.
Amendment dated Feb. 2, 2004 in Reply to Office Action dated Jul. 29, 2003 for U.S. Appl. No. 09/990,909.
Amendment dated Feb. 29, 2008 in Reply to Notice of Non-Responsive Amendment dated Feb. 11, 2008 for U.S. Appl. No. 11/555,697.
Amendment dated Feb. 7, 2003 in Reply to Office Action dated Jul. 30, 2002 for U.S. Appl. No. 09/990,909.
Amendment dated Feb. 7, 2009 in Reply to Office Action dated Aug. 18, 2008 for U.S. Appl. No. 10/681,018.
Amendment dated Mar. 1, 2004 in Reply to Office Action dated Aug. 26, 2003 for U.S. Appl. No. 10/041,073.
Amendment dated Mar. 24, 2010 in Reply to Final Office Action dated Jul. 2, 2010 for U.S. Appl. No. 12/046,252.
Amendment dated Mar. 3, 2008 to Restriction Requirement dated Jan. 10, 2008 for U.S. Appl. No. 11/232,180.
Amendment dated Mar. 4, 2008 in Reply to Office Action dated Nov. 14, 2007 for U.S. Appl. No. 11/213,255.
Amendment dated May 18, 2007 in Reply to Office Action dated Dec. 22, 2006 for U.S. Appl. No. 10/681,018.

(56) References Cited

OTHER PUBLICATIONS

Amendment dated May 19, 2008 in Reply to Final Office Action dated Mar. 17, 2008 for U.S. Appl. No. 10/681,018.
Amendment dated May 27, 2009 in Reply to Final Office Action dated Feb. 27, 2009 for U.S. Appl. No. 11/555,697.
Amendment dated Jun. 15, 2009 in Reply to Final Office Action dated Mar. 13, 2009 for U.S. Appl. No. 11/232,180.
Amendment dated Jun. 8, 2007 in Reply to Restriction Requirement dated May 9, 2007 for U.S. Appl. No. 11/213,382.
Amendment dated Jun. 8, 2010 in Reply to Office Action dated Jan. 8, 2010 for U.S. Appl. No. 10/681,018.
Blackmer. Parkinson disease: treatment and medication. Mar. 10, 2009., retrieved from the internet on Sep. 15, 2009, http://emedicine.medscape.com/article/312519-treatment.
Bode et al. Usefulness of a simple photometric determination of chymotrypsin activity in stools—results of a multicentre study. Clin Biochem. 1986; 19:333-37.
Brudnak et al. Enzyme-based therapy for autism spectrum disorders—is it worth another look? Med Hypoth. 2002; 58:422-428.
Campbell et al. A genetic variant that disrupts MET transcription is associated with autism. Proc Natl Acad Sci USA. 2006; 103(45):16834-16839.
Carlton. Autism and malnutrition: the milk connection. Retrieved from the internet on Feb. 18, 2008, http://www.mercola.com/2004/autism_malnutrition.htm.
Cruse et al. Illustrated dictionary of immunology. CRC Press, New York. 1995.
Darman. An introduction to alternative medicine for psychiactric conditions. Oct. 22, 2007, retrieved on Sep. 18, 2009, http://web.archive.org/web/20071022104238/http://altp[therapies4bipolar.info/ortho/html.
Digestive Enzyme,' retrieved from the internet Sep. 10, 2009, http://en.wikipedia.org/wiki/Digestive_enzyme.
Dockter et al. Determination of chymotrypsin in the feces by a new photometric method. Padiatr Padol. 1985; 20(3):257-265.
Filipek et al. The screening and diagnosis of autistic spectrum disorders. J. of Autism and Dev Disorders. 1999; 29(6).
Final Office Action dated Nov. 9, 2010 for U.S. Appl. No. 09/990,909.
Final Office Action dated Feb. 14, 2011 for U.S. Appl. No. 12/049,613.
Final Office Action dated Feb. 27, 2009 for U.S. Appl. No. 11/555,697.
Final Office Action dated Mar 13, 2008 for U.S. Appl. No. 11/232,180.
Final Office Action dated Mar. 17, 2008 for U.S. Appl. No. 10/681,018.
Final Office Action dated Apr. 28, 2009 for U.S. Appl. No. 10/681,018.
Final Office Action dated May 11, 2010 for U.S. Appl. No. 11/555,697.
Final Office Action dated Jun. 25, 2008 for U.S. Appl. No. 11/213,255.
Final Office Action dated Jul. 2, 2010 for U.S. Appl. No. 12/046,252.
Final Office Action dated Jul. 27, 2004 for U.S. Appl. No. 09/990,909.
Finegold et al. Gastrointestinal microflora studies in late-onset autism. Clinical Infectious Diseases. 2002; 35(1):S6-S15.
Garcia et al. Detection of *Giardia lamblia*, *Entamoeba histolytica/Entamoeba dispar*, and *Cryptosporidium parvum* antigens in human fecal specimens using the triage parasite panel enzyme immunoassay. Am Soc for Microbiology. 2000; 38(9):3337-3340.
Happe et al. The neuropsychology of autism. Brain. 1996; 119:1377-1400.
Happe et al. Time to give up on a simple explanation for autism. Nat Neurosci. Oct. 2006; 9(10):1218-20.
Hendren et al. Mechanistic biomarkers for autism treatment. Medical Hypotheses. 2009; 73:950-954.
Horvath et al. Improved social and language skills after secretin administration in patients with autistic spectrum disorders. Journal of the Association for Academic Minority Physicians. Jan. 1998; 9(1):9-15.
Nachaegari et al. Coprocessed excipients for solid dosage forms. Pharmaceutical Technology. 2004; p. 52, 54, 56 ,58, 60, 64.
Nevo et al. Acute immune polyneuropathies: correlations of serum antibodies to *Campylobacter jejuni* and *Helicobacter pylori* with anti-gm antibodies and clinical patterns of disease. J of Inf diseases. 1997; 175(S2):S154-6.
Ninds Dysautonimia Information Page, retrieved from the internet Sep. 10, 2009, http://www.ninds.nih.gov/disorders/dysautonomia/dysautonomia.htm.
Ninds Guillain-Barre Syndrome Information Page, retrieved from the internet Sep. 15, 2009, http://www.ninds.nih.gov/disorders/gbs/gbs.htm.
Notice Non-Compliant Amendment dated Jun. 19, 2009 for U.S. Appl. No. 11/232,180.
Notice Non-responsive Amendment dated Sep. 22, 2008 for U.S. Appl. No. 11/232,180.
Notice of Non-Complaint Amendment dated Jun. 2, 2008 for U.S. Appl. No. 12/046,252.
Notice of Non-Compliant Amendment dated Apr. 27, 2010 for U.S. Appl. No. 12/283,090.
Notice of Non-Compliant Amendment dated May 7, 2007 for U.S. Appl. No. 11/213,255.
Notice of Non-Responsive Amendment dated Feb. 11, 2008 for U.S. Appl. No. 11/555,697.
Notice of Non-Responsive Amendment dated Sep. 25, 2008 for U.S. Appl. No. 11/555,697.
Office Action dated Jan. 21, 2011 for U.S. Appl. No. 12/386,051.
Office Action dated Jan. 29, 2002 for U.S. Appl. No. 09/707,395.
Office Action dated Jan. 8, 2010 for U.S. Appl. No. 10/681,018.
Office Action dated Oct. 1, 2001 for U.S. Appl. No. 09/466,559.
Office Action dated Oct. 5, 2010 for U.S. Appl. No. 12/046,402.
Office Action dated Nov. 14, 2007 for U.S. Appl. No. 11/213,255.
Office Action dated Nov. 15, 2010 for U.S. Appl. No. 12/238,415.
Office Action dated Nov. 25, 2009 for U.S. Appl. No. 11/232,180.
Office Action dated Nov. 26, 2001 for U.S. Appl. No. 09/466,559.
Office Action dated Dec. 19, 2005 for U.S. Appl. No. 10/730,567.
Office Action dated Dec. 22, 2006 for U.S. Appl. No. 10/681,018.
Office Action dated Mar. 18, 2008 for U.S. Appl. No. 11/468,379.
Office Action dated Mar. 25, 2008 for U.S. Appl. No. 11/213,382.
Office Action dated Mar. 28, 2008 for U.S. Appl. No. 11/555,697.
Office Action dated Apr. 12, 2010 for U.S. Appl. No. 09/990,909.
Office Action dated Apr. 21, 2008 for U.S. Appl. No. 11/232,180.
Office Action dated Apr. 22, 2003 for U.S. Appl. No. 09/929,592.
Office Action dated May 22, 2002 for U.S. Appl. No. 09/466,559.
Office Action dated Jun. 30, 2004 for U.S. Appl. No. 10/730,567.
Office Action dated Jul. 22, 2010 for U.S. Appl. No. 12/049,613.
Office Action dated Jul. 29, 2003 for U.S. Appl. No. 09/990,909.
Office Action dated Jul. 30, 2002 for U.S. Appl. No. 09/707,395.
Office Action dated Jul. 30, 2002 for U.S. Appl. No. 09/990,909.
Office Action dated Jul. 6, 2010 for U.S. Appl. No. 11/533,818.
Office Action dated Aug. 13, 2002 for U.S. Appl. No. 09/929,592.
Office Action dated Aug. 18, 2008 for U.S. Appl. No. 10/681,018.
Office Action dated Aug. 18, 2010 for U.S. Appl. No. 10/681,018.
Office Action dated Aug. 20, 2010 for U.S. Appl. No. 12/283,090.
Office Action dated Aug. 25, 2010 for U.S. Appl. No. 12/487,868.
Office Action dated Aug. 26, 2003 for U.S. Appl. No. 10/041,073.
Office Action dated Aug. 3, 2009 for U.S. Appl. No. 11/555,697.
Office Action dated Aug. 7, 2007 for U.S. Appl. No. 10/681,018.
Office Action dated Aug. 8, 2007 for U.S. Appl. No. 11/213,382.
Office Action dated Sep. 22, 2004 for U.S. Appl. No. 10/730,567.
Office Action dated Sep. 24, 2009 for U.S. Appl. No. 12/046,252.
Pancreatic Enzyme Concentrate (PEC) Undiluted, Technical Data Sheet. 1 page, Scientific Protein Laboratories LLC Jun. 13, 2005.
Pancreatin 4X USP, Technical Data Sheet, 1 page, Scientific Protein laboratories LLC Jun. 13, 2005.
Parisi et al. Evaluation of new rapid commercial enzyme immunoassay for detection of *Crytosporidium oocysts* in untreated stool specimens. J Clin Microbiol. 1995; 33(7):1963-1965.

(56) References Cited

OTHER PUBLICATIONS

Perman et al. Role of ph in production of hydrogen from carbohydrates by colonic bacterial flora. J Clin Invest. 1981; 24(4):684-685.
Peters et al. Prevalence of enteric parasites in homosexual patients attending an outpatient clinic. J of Clin Micro. 1986; 24(4):684-685.
Preliminary Amendment dated May 18, 2009 for U.S. Appl. No. 12/046,252.
Remtulla et al. Stool chymotrypsin activity measured by a spectrophotometric procedure to identify pancreat disease in infants. Clinical Biochemistry. Dec. 1996; 19:341-342.
Response dated Oct. 3, 2006 to Restriction Requirement dated Sep. 12, 2006 for U.S. Appl. No. 10/681,018.
Response dated Apr. 29, 2010 to Notice of Non-Compliant Amendment dated Apr. 27, 2010 for U.S. Appl. No. 12/283,090.
Response dated Jun. 17, 2008 to Advisory Action dated Jun. 3, 2008 for U.S. Appl. No. 10/681,018.
Response dated Jun. 24, 2002 to Restriction Requirement dated May 22, 2002 for U.S. Appl. No. 09/990,909.
Response dated Jun. 7, 2007 to Notice of Non-Compliant Amendment dated May 7, 2007 for U.S. Appl. No. 11/213,255.
Restriction Requirement dated Jan. 10, 2008 for U.S. Appl. No. 11/232,180.
Restriction Requirement dated Jan. 13, 2010 for U.S. Appl. No. 12/487,868.
Restriction Requirement dated Oct. 17, 2007 for U.S. Appl. No. 11/555,697.
Restriction Requirement dated Oct. 7, 2009 for U.S. Appl. No. 12/283,090.
Restriction Requirement dated Dec. 10, 2009 for U.S. Appl. No. 11/533,818.
Restriction Requirement dated Apr. 23, 2003 for U.S. Appl. No. 09/990,909.
Restriction Requirement dated May 22, 2002 for U.S. Appl. No. 09/990,909.
Restriction Requirement dated May 9, 2007 for U.S. Appl. No. 11/213,382.
Restriction Requirement dated Jun. 22, 2007 for U.S. Appl. No. 11/213,255.
Restriction Requirement dated Sep. 12, 2006 for U.S. Appl. No. 10/681,018.
Rogers. No more heartburn: Stop the pain in 30 days—naturally. 2000; 172.
Sandler et al. Short term benefit from oral vancomycin treatment of regressive-onset autism. J of Child Neuro. 2000; 15(7):42-435.
Schiller. Review article: the therapy of constipation. Aliment Pharmacol Ther. 2001; 15:749-763.
Schreck et al. Food preferences and factors influecing food selectivity for children with autism spectrum disorders. Res Develop Disabil. 2006; 27:353-363.
Seneca et al. Enhancement of brain 1-dopa concetration with a-chymotrypsm. J American Geriatrics Society. 1973; 256-258.
Sherwood et al. A new class of high-functionality excipients: silicified microcrystalline cellulose. Pharm Tech. 1998; 22(10):78-88.
Skeels et al. *Crytosporidium* infection in Oregon public health clinic patients 1985-88: the value of statewide laboratory surveillance. AJPH. 1990; 80(3):305-308.
Stein, et a. Nitrogen Metabolism in normal and hyperkinetic boys. Am J Clin Nutr. 1984; 39:520-524.
Supplemental Amendment and Response dated Jun. 8, 2010 to Restriction Requirement dated Oct. 7, 2009 for U.S. Appl. No. 12/283,090.
The Alzheimer's Association. Basics of Alzheimer's Disease. 2005, http://www.alz.org/national/documents/brochure_Basicsofalz_low/pdf.
Tsang et al. Extragastroduodenal conditions associated with *Heliobacter pylori* infection. Hong Kong Medical Journal. 1999; 5(2):169-174.
USP (32)-NF(27) 2009, Pancreatin, V.3, pp. 3194-3195.
Wender et al. Prevalence of attention deficit disorder, residual type, and other psychiatric disorders in patients with irritable colon syndrome. Am J Psychiatry. 1983; 140(12):1579-82 Abstract only.
Wohlman et al. Enhancement of drug activity by chymotrypsin, penicillin penetration into granulomatous sesions and inflammatory fluids. Cellular and Molecular Life Sciences. 1969; 25(9):953-954.
Woodward et al. Ischaemic enterocolitis complicating aidiopathic dysatuonomia. Gut. 1998; 43:285-287.
Zhang et al. Lactulose-mannitol intestinal permeability test in children with diarrhea caused by rotavirus abd *Cryptosporidium*. J of Pediatric Gastro & Nutrition. 2000; 31(1):16-21.
ABCnews. Changing Face of Autism: Numbers Rise as More Behaviors Included. ABCnews. Nov. 1, 2007.
Aman, et al. Outcome measures for clinical drug trials in autism. CNS Spectr. Jan. 2004;9(1):36-47.
Amendment dated Mar. 24, 2010 in Reply to Final Office Action dated Sep. 24, 2009 for U.S. Appl. No. 12/046,252.
Ang, et al. Biological role and regulation of the universally conserved heat shock proteins. J Biol Chem. Dec. 25, 1991;266(36):24233-6.
Arribas, et al. A comparative study of the chymotrypsin-like activity of the rat liver multicatalytic proteinase and the ClpP from *Escherichia coli*. J Biol Chem. Oct. 5, 1993;268(28):21165-71.
Arrigo, et al. Expression of heat shock proteins during development in *Drosophila*. Results Probl Cell Differ. 1991;17:106-19.
ASH. Patient Information Guide—Understanding Hypertension. American Society of Hypertension. 2004. 1-7.
Ashwood, et al. Immune activation of peripheral blood and mucosal CD3+ lymphocyte cytokine profiles in children with autism and gastrointestinal symptoms. J Neuroimmunol. Dec. 19, 2005; 1-9.
Ashwood, et al. Intestinal lymphocyte populations in children with regressive autism: evidence for extensive mucosal immunopathology. J Clin Immunol. Nov. 2003;23(6):504-17.
Ashwood, et al. Spontaneous mucosal lymphocyte cytokine profiles in children with autism and gastrointestinal symptoms: mucosal immune activation and reduced counter regulatory interleukin-10. J Clin Immunol. Nov. 2004;24(6):664-73.
Austic. Development and adaptation of protein digestion. J Nutr. May 1985;115(5):686-97.
Autism Diagnosis. Autism Statistics. Www.autism-diagnosis.com/autism_statistics/autism_statistics.html. 2007.
Awazuhara, et al. Antigenicity of the proteins in soy lecithin and soy oil in soybean allergy. Clin Exp Allergy. Dec. 1998;28(12):1559-64.
Axcan Pharma Inc. Cdn Prescribing Information on VIOKASE Pancrelipase, USP tablets, powder. 2000: 1-3.
Bailey, et al. Co-occurring conditions associated with FMR1 gene variations: findings from a national parent survey. Am J Med Genet A. Aug. 15, 2008;146A(16):2060-9.
Bakkaloglu, et al. Atopic features in early childhood autism. Eur J Paediatr Neurol. Nov. 2008;12(6):476-9.
Barnhart, et al. Symptomatic granular cell tumor involving the pituitary gland in a dog: a case report and review of the literature. Vet Pathol. May 2001;38(3):332-6.
Beilmann, et al. Neoexpression of the c-met/hepatocyte growth factor-scatter factor receptor gene in activated monocytes. Blood. Dec. 1, 1997;90(11):4450-8.
Bellanti, et al. Abnormalities of Th1 function in non-IgE food allergy, celiac disease, and ileal lymphonodular hyperplasia: a new relationship? Ann Allergy Asthma Immunol. Jun. 2003;90(6 Suppl 3):84-9.
Berg, et al. Section 10.5 Many Enzymes are Actived by Specific Proteolytic Cleavage. 2002.
Berg, et al. Section 9.1 Proteases: Facilitating a Difficult Reaction. 2002.
Berg, et al. Table of Contents. Biochemistry, 5th edition. 2002.
Birnbaum, et al. Heat shock or stress proteins and their role as autoantigens in multiple sclerosis. Ann N Y Acad Sci. Dec. 19, 1997;835:157-67. Abstract only.
BLOG. Acid Phosphatase Research (blog). Acid-phosphatase. blogspot.com. 2008.
Boorom. Is this recently characterized gastrointestinal pathogen responsible for rising rates of inflammatory bowel disease (IBD) and IBD associated autism in Europe and the United States in the 1990s? Med Hypotheses. 2007;69(3):652-9.

(56) References Cited

OTHER PUBLICATIONS

Borowitz, et al. Use of pancreatic enzyme supplements for patients with cystic fibrosis in the context of fibrosing colonopathy. Consensus Committee. J Pediatr. Nov. 1995;127(5):681-4.
Boyd, et al. Positively charged amino acid residues can act as topogenic determinants in membrane proteins. Proc Natl Acad Sci U S A. Dec. 1989;86(23):9446-50.
Bradstreet, et al. Detection of Measles Virus Genomic RNA in Cerebrospinal Fluid of Children with Regressive Autism: a Report of Three Cases. J. Am Phys Surg. 2004; 9(2):38-45.
Bruhat, et al. Amino acid limitation induces expression of CHOP, a CCAAT/enhancer binding protein-related gene, at both transcriptional and post-transcriptional levels. J Biol Chem. Jul. 11, 1997;272(28):17588-93.
Campbell, et al. Distinct genetic risk based on association of MET in families with co-occurring autism and gastrointestinal conditions. Pediatrics. Mar. 2009;123(3):1018-24.
Caronna, et al. Autism spectrum disorders: clinical and research frontiers. Arch Dis Child. Jun. 2008;93(6):518-23.
Carroccio, et al. Secondary impairment of pancreatic function as a cause of severe malabsorption in intestinal giardiasis: a case report. Am J Trop Med Hyg. Jun. 1997;56(6):599-602.
Carroccio, et al. Secretin-cerulein test and fecal chymotrypsin concentration in children with intestinal giardiasis. Int J Pancreatol. Oct. 1993;14(2):175-80.
Cassidy, et al. A new concept for the mechanism of action of chymotrypsin: the role of the low-barrier hydrogen bond. Biochemistry. Apr. 15, 1997;36(15):4576-84.
CDC. Attention-Deficit/Hyperactivity Disorder (ADHD). Www.cdc.org. 2005.
CDC. Autism Information Center/FAQs. Dept of Health and Human Services/CDC. Jan. 30, 2008.
Chen, et al. Identification of two lysosomal membrane glycoproteins. J Cell Biol. Jul. 1985;101(1):85-95.
Chen, et al. Lysine 43 is trimethylated in subunit C from bovine mitochondrial ATP synthase and in storage bodies associated with batten disease. J Biol Chem. May 21, 2004;279(21):21883-7.
Cichoke, et al. The complete book of enzyme therapy. Penguin. 1998: 39, 42, 47, 50, and 53.
Claud, et al. Hypothesis: inappropriate colonization of the premature intestine can cause neonatal necrotizing enterocolitis. FASEB J. Jun. 2001;15(8):1398-403.
Corring, et al. Development of digestive enzymes in the piglet from birth to 8 weeks. I. Pancreas and pancreatic enzymes. Nutr Metab. 1978;22(4):231-43.
Couet, et al. Identification of peptide and protein ligands for the caveolin-scaffolding domain. Implications for the interaction of caveolin with caveolae-associated proteins. J Biol Chem. Mar. 7, 1997;272(10):6525-33.
Coyle. Treating the Negative Symptoms of Schizophrenia: An Expert Interview with Joseph Coyle, MD. www.narsad.org/?q=node/438/latest-research. 2006.
Craig, et al. Heat shock proteins: molecular chaperones of protein biogenesis. Microbiol Rev. Jun. 1993;57(2):402-14.
Croonenberghs, et al. Peripheral markers of serotonergic and noradrenergic function in post-pubertal, caucasian males with autistic disorder. Neuropsychopharmacology. Mar. 2000;22(3):275-83.
Cuervo, et al. Cathepsin a regulates chaperone-mediated autophagy through cleavage of the lysosomal receptor. EMBO J. Jan. 2, 2003;22(1):47-59.
Dawe, et al. The chakragati mouse: a mouse model for rapid in vivo screening of antipsychotic drug candidates. Biotechnol J. Nov. 2007;2(11):1344-52.
DAWN. Autism: the Latest Prevalence Rates in USA—Now 1 in 175. Disabled Women's Network Ontario. Dawn.thot.net/autism2.html. 2006.
Dawson lab. Research Projects in Synthetic Protein Chemistry. 2005; 1-2.
Derwent. Abstract for RU 2286785 Nov. 10, 2006. Downloaded from the Derwent file Jul. 13, 2011.

Diaz-Hernandez, et al. Neuronal induction of the immunoproteasome in Huntington's disease. J Neurosci. Dec. 17, 2003;23(37):11653-61.
Ding, et al. Proteasome inhibition in oxidative stress neurotoxicity: implications for heat shock proteins. J Neurochem. May 2001;77(4):1010-7.
Edelson, et al. 3-Cyclohexene-1-glycine, an Isoleucine Antagonist. J. Am. Chem. Soc. 1958; 80(11):2698-2700.
Elphick, et al. Impaired luminal processing of human defensin-5 in Crohn's disease: persistence in a complex with chymotrypsinogen and trypsin. Am J Pathol. Mar. 2008;172(3):702-13.
Ethridge, et al. Acute pancreatitis results in induction of heat shock proteins 70 and 27 and heat shock factor-1. Pancreas. Oct. 2000;21(3):248-56.
Fafournoux, et al. Amino acid regulation of gene expression. Biochem J. Oct. 1, 2000;351(Pt 1):1-12.
Fallingborg, et al. Measurement of gastrointestinal pH and regional transit times in normal children. J Pediatr Gastroenterol Nutr. Aug. 1990;11(2):211-4.
Fernell, et al. No evidence for a clear link between active intestinal inflammation and autism based on analyses of faecal calprotectin and rectal nitric oxide. Acta Paediatr. Jul. 2007;96(7):1076-9.
Fitzsimmons, et al. High-dose pancreatic-enzyme supplements and fibrosing colonopathy in children with cystic fibrosis. N Engl J Med. May 1, 1997;336(18):1283-9.
Frossard, et al. Both thermal and non-thermal stress protect against caerulein induced pancreatitis and prevent trypsinogen activation in the pancreas. Gut. Jan. 2002;50(1):78-83.
Frossard. Trypsin activation peptide (TAP) in acute pancreatitis: from pathophysiology to clinical usefulness. JOP. Mar. 2001;2(2):69-77.
Furlano, et al. Colonic CD8 and gamma delta T-cell infiltration with epithelial damage in children with autism. J Pediatr. Mar. 2001;138(3):366-72.
Gardner. Absorption of intact peptides: studies on transport of protein digests and dipeptides across rat small intestine in vitro. Q J Exp Physiol. Oct. 1982;67(4):629-37.
Garner Jr, et al. Porcine Pancreatic Lipase—A Glycoprotein. J Biol Chem. Jan. 25, 1972;247(2):561-5.
Gass, et al. Enhancement of dietary protein digestion by conjugated bile acids. Gastroenterology. Jul. 2007;133(1):16-23.
Giglio, et al. Failure to thrive: the earliest feature of cystic fibrosis in infants diagnosed by neonatal screening. Acta Paediatr. Nov. 1997;86(11):1162-5.
Goff, et al. Production of abnormal proteins in E. coli stimulates transcription of lon and other heat shock genes. Cell. Jun. 1985;41(2):587-95.
Gonzalez, et al. Endoscopical, histological and immunological characteristics of the digestive mucosa in autistic children with gastrointestinal symptoms. 2005; 1-7.
Green, et al. Amino-terminal polymorphisms of the human beta 2-adrenergic receptor impart distinct agonist-promoted regulatory properties. Biochemistry. Aug. 16, 1994;33(32):9414-9.
Gupta, et al. Th1- and Th2-like cytokines in CD4+ and CD8+ T cells in autism. J Neuroimmunol. May 1, 1998;85(1):106-9.
Hadjivassiliou, et al. Does cryptic gluten sensitivity play a part in neurological illness? Lancet. Feb. 10, 1996;347(8998):369-71.
Health.com. Who is affected by Parkinson's disease. www.health.com. Jul. 14, 2008.
Heijerman, et al. Omeprazole enhances the efficacy of pancreatin (pancrease) in cystic fibrosis. Ann Intern Med. Feb. 1, 1991;114(3):200-1.
Hitti. Allergy, celiac disease, and ileal lymphonodular. WebMD. 2005. 1-2.
Horvath, et al. Autistic disorder and gastrointestinal disease. Curr Opin Pediatr. Oct. 2002;14(5):583-7.
Horvath, et al. Gastrointestinal abnormalities in children with autistic disorder. J Pediatr. Nov. 1999;135(5):559-63.
Houston. Autism—One Conference. May 2006. 1-83.
Hsiao, et al. The microbes of the intestine: an introduction to their metabolic and signaling capabilities. Endocrinol Metab Clin North Am. Dec. 2008;37(4):857-71.

(56) References Cited

OTHER PUBLICATIONS

Huang, et al. Apoptotic cell death in mouse models of GM2 gangliosidosis and observations on human Tay-Sachs and Sandhoff diseases. Hum Mol Genet. Oct. 1997;6(11):1879-85.
Huang, et al. Mapping of the human APOB gene to chromosome 2p and demonstration of a two-allele restriction fragment length polymorphism. Proc Natl Acad Sci U S A. Feb. 1986;83(3):644-8.
James, et al. Thimerosal neurotoxicity is associated with glutathione depletion: protection with glutathione precursors. Neurotoxicology. 2004; 26(1):1-8.
Juhl. Fibromyalgia and the serotonin pathway. Altern Med Rev. 1998; 3(5):367-375.
Jyonouchi, et al. Dysregulated innate immune responses in young children with autism spectrum disorders: their relationship to gastrointestinal symptoms and dietary intervention. Neuropsychobiology. 2005;51(2):77-85.
Jyonouchi, et al. Evaluation of an association between gastrointestinal symptoms and cytokine production against common dietary proteins in children with autism spectrum disorders. J Pediatr. May 2005;146(5):605-10.
Jyonouchi, et al. Proinflammatory and regulatory cytokine production associated with innate and adaptive immune responses in children with autism spectrum disorders and developmental regression. J Neuroimmunol. Nov. 1, 2001;120(1-2):170-9.
Kachrimanis, et al. Tensile strength and disintegration of tableted silicified microcrystalline cellulose: influences of interparticle bonding. J Pharm Sci. Jul. 2003;92(7):1489-501.
Kaemmerer, et al. Effects of lipid peroxidation-related protein modifications on RPE lysosomal functions and POS phagocytosis. Invest Ophthalmol Vis Sci. Mar. 2007;48(3):1342-7.
Kaminski, et al. Polymorphism of bovine beta-casein and its potential effect on human health. J Appl Genet. 2007;48(3):189-98.
Kearney, et al. Global burden of hypertension: analysis of worldwide data. Lancet. Jan. 15-21, 2005;365(9455):217-23. Abstract only.
Knivsberg, et al. A randomised, controlled study of dietary intervention in autistic syndromes. Nutr Neurosci. Sep. 2002;5(4):251-61.
Koller, et al. Falls and Parkinson's Disease (Abstract). Clin Neuropharmacol. 1989; 12(2):98-105.
Kujoth, et al. Mitochondrial DNA mutations, oxidative stress, and apoptosis in mammalian aging. Science. Jul. 15, 2005;309(5733):481-4.
Levy, et al. Relationship of dietary intake to gastrointestinal symptoms in children with autistic spectrum disorders. Biol Psychiatry. Feb. 15, 2007;61(4):492-7.
Leyfer, et al. Comorbid psychiatric disorders in children with autism: interview development and rates of disorders. J Autism Dev Disord. Oct. 2006;36(7):849-61.
Lloyd. Lysosome membrane permeability: implications for drug delivery. Adv Drug Deliv Rev. Mar. 30, 2000;41(2):189-200.
Loh, et al. Highly tolerated amino acid substitutions increase the fidelity of *Escherichia coli* DNA polymerase I. J Biol Chem. Apr. 20, 2007;282(16):12201-9.
Lord, et al. Diagnostic Instruments in Autistic Spectrum Disorders. info.med.yale.edu. 2005; 11:730-771.
Luedtke, et al. Cathepsin A is expressed in a cell- and region-specific manner in the testis and epididymis and is not regulated by testicular or pituitary factors. J Histochem Cytochem. Aug. 2000;48(8):1131-46.
MacFabe, et al. Neurobiological effects of intraventricular propionic acid in rats: possible role of short chain fatty acids on the pathogenesis and characteristics of autism spectrum disorders. Behav Brain Res. 2006;176(1):149-69.
Mannino, et al. Surveillance for asthma—United States, 1960-1995. MMWR CDC Surveill Summ. Apr. 24, 1998;47(1):1-27.
Maurin, et al. Cellular adaptation to amino acid availability: mechanisms involved in the regulation of gene expression. 2006; 319-326.
McAlonan, et al. Brain anatomy and sensorimotor gating in Asperger's syndrome. ain. Jul. 2002;125(Pt 7):1594-606.
McCormack, et al. Localization of the disulfide bond involved in post-translational processing of glycosylasparaginase and disrupted by a mutation in the Finnish-type aspartylglycosaminuria. J Biol Chem. Feb. 17, 1995;270(7):3212-5.
McCracken, et al. Risperidone in children with autism and serious behavioral problems. N Engl J Med. Aug. 1, 2002;347(5):314-21.
Minamino, et al. Vascular cell senescence: contribution to atherosclerosis. Circ Res. Jan. 5, 2007;100(1):15-26.
Ming, et al. Autism spectrum disorders: concurrent clinical disorders. J Child Neurol. Jan. 2008;23(1):6-13.
Mitchell, et al. Comparative trial of viokase, pancreatin and Pancrease pancrelipase (enteric coated beads) in the treatment of malabsorption in cystic fibrosis. Aust Paediatr J. Jun. 1982;18(2):114-7.
Mononen, et al. Aspartylglycosaminuria in the Finnish population: identification of two point mutations in the heavy chain of glycoasparaginase. Proc Natl Acad Sci U S A. Apr. 1, 1991;88(7):2941-5.
Nagamoto. Jacobson: Psychiatric Secrets, 2nd ed. 2001.
Neuer, et al. The role of heat shock proteins in reproduction. Hum Reprod Update. Mar.-Apr. 2000;6(2):149-59.
Notice of Allowance dated Apr. 15, 2011 for U.S. Appl. No. 12/487,868.
Notice of Allowance dated Apr. 29, 2011 for U.S. Appl. No. 12/046,402.
Notice of Allowance dated May 23, 2011 for U.S. Appl. No. 09/990,909.
Notice of Allowance dated Jun. 27, 2011 for U.S. Appl. No. 12/238,415.
Notice of Allowance dated Jun. 28, 2011 for U.S. Appl. No. 12/487,868.
Notice of Allowance dated Jun. 30, 2011 for U.S. Appl. No. 09/990,909.
Notice of Allowance dated Jul. 8, 2011 for U.S. Appl. No. 12/046,402.
Notice of Allowance dated Aug. 8, 2011 for U.S. Appl. No. 12/426,794.
Office Action dated Mar. 29, 2011 for U.S. Appl. No. 12/054,343.
Office Action dated Mar. 30, 2011 for U.S. Appl. No. 12/786,739.
Office Action dated Apr. 27, 2011 for U.S. Appl. No. 10/681,018.
Office Action dated Apr. 28, 2011 for U.S. Appl. No. 12/283,090.
Office Action dated May 24, 2011 for U.S. Appl. No. 12/487,864.
Office action dated Jun. 29, 2011 for U.S. Appl. No. 11/555,697.
Owley, et al. Multisite, double-blind, placebo-controlled trial of porcine secretin in autism. J Am Acad Child Adolesc Psychiatry. Nov. 2001;40(11):1293-9.
Park, et al. Increased apoptosis in cystinotic fibroblasts and renal proximal tubule epithelial cells results from cysteinylation of protein kinase Cdelta. J Am Soc Nephrol. Nov. 2006;17(11):3167-75.
Parkinsons Disease Foundation. Parkinson's Disease Q&A. 2007. 1-44.
Parkinsons Disease Foundation. Ten Frequently-Asked Questions about Parkinson's Disease. 2006.
Parracho, et al. Differences between the gut microflora of children with autistic spectrum disorders and that of healthy children. J Med Microbiol. Oct. 2005;54(Pt 10):987-91.
Persico, et al. Searching for ways out of the autism maze: genetic, epigenetic and environmental clues. Trends Neurosci. Jul. 2006;29(7):349-58.
Polanczyk, et al. The worldwide prevalence of ADHD: a systematic review and metaregression analysis. Am J Psychiatry. Jun. 2007;164(6):942-8.
Ponsky, et al. Alterations in gastrointestinal physiology after Roux-en-Y gastric bypass. J Am Coll Surg. Jul. 2005;201(1):125-31.
Puri, et al. Isolated segmental duodenal ganglionosis. Indian Journal of Radiology and Imaging. 2000; 153-154.
Raimondo, et al. Rapid endoscopic secretin simulation test and discrimination of chronic pancreatisis and pancreatic cancer from disease controls. Clin Gastroenterol Hepatol. Sep. 2003;1(5):397-403.
Rakonczay, et al. A new severe acute necrotizing pancreatitis model induced by L-ornithine in rats. Crit Care Med. Jul. 2008;36(7):2117-27.
Ray, et al. Growth factor regulation of enterocyte nutrient transport during intestinal adaptation. Am J Surg. Apr. 2002;183(4):361-71.

(56) References Cited

OTHER PUBLICATIONS

Rider, et al. Perspective of biochemical research in the neuronal ceroid-lipofuscinosis. Am J Med Genet. Feb. 15, 1992;42(4):519-24.
Rottier, et al. Lack of PPCA expression only partially coincides with lysosomal storage in galactosialidosis mice: indirect evidence for spatial requirement of the catalytic rather than the protective function of PPCA. Hum Mol Genet. Oct. 1998;7(11):1787-94.
Rubenstein, et al. Model of autism: increased ratio of excitation/inhibition in key neural systems. Genes Brain Behav. Oct. 2003;2(5):255-67.
Sandler, et al. Lack of benefit of a single dose of synthetic human secretin in the treatment of autism and pervasive developmental disorder. N Engl J Med. Dec. 9, 1999;341(24): 1801-6.
Schafer, et al. Stress kinases and heat shock proteins in the pancreas: possible roles in normal function and disease. J Gastroenterol. 2000;35(1):1-9.
Schneider, et al. Oral human immunoglobulin for children with autism and gastrointestinal dysfunction: a prospective, open-label study. J Autism Dev Disord. Nov. 2006;36(8):1053-64.
Schreck, et al. Food preferences and factors influencing food selectivity for children with autism spectrum disorders. Res Dev Disabil. 2005;27(4):353-63.
Settembre, et al. A block of autophagy in lysosomal storage disorders. Hum Mol Genet. Jan. 1, 2008;17(1):119-29.
Shaul. Report to the Chairman and Ranking Minority Member, Subcommittee on Human Rights and Wellness, Committee on Government Reform, House of Representatives. GEO. Jan. 2005. 1-40.
Sherwood, et al. Activation of trypsinogen in large endocytic vacuoles of pancreatic acinar cells. Proc Natl Acad Sci U S A. Mar. 27, 2007;104(13):5674-9.
Shimabukuro, et al. Medical expenditures for children with an autism spectrum disorder in a privately insured population. J Autism Dev Disord. 2007;38(3):546-52.
Shpacovitch, et al. Protease-activated receptors: novel PARtners in innate immunity. Trends Immunol. Dec. 2007;28(12):541-50.
Singh, et al. Plasma increase of interleukin-12 and interferon-gamma. Pathological significance in autism. J Neuroimmunol. May 1996;66(1-2):143-5.
Smith, et al. Fecal chymotrypsin and trypsin determinations. Canadian Medical Association Journal. 1971; 104(8):691-4 and 697.
Statemaster. Number of Children with Autism (most recent w/graph) by state. Statemaster.com Jul. 14, 2008.
Statemaster. Number of Children with Autism (most recent) by state. Statemaster.com Jul. 14, 2008.
Statemaster. Number of Children with Autism (per capita)(most recent) by state. Statemaster.com Jul. 14, 2008.
Stein, et al. Nitrogen metabolism in normal and hyperkinetic boys. Am J Clin Nutr. Apr. 1984;39(4):520-4.
Steinherz, et al. Patterns of amino acid efflux from isolated normal and cystinotic human leucocyte lysosomes. J Biol Chem. Jun. 10, 1982;257(11):6041-9.
Stoll, et al. Enteral nutrient intake level determines intestinal protein synthesis and accretion rates in neonatal pigs. Am J Physiol Gastrointest Liver Physiol. Aug. 2000;279(2):G288-94.
Stott, et al. MMR and Autism in Perspective: the Denmark Story. J. Am Phys Surg. 2004; 9(3):89-91.
Strader, et al. Publication Structural basis of β-adrenergic receptor function. FASEB J. May 1989;3(7):1825-32.
Sturmey. Secretin is an ineffective treatment for pervasive developmental disabilities: a review of 15 double-blind randomized controlled trials. Res Dev Disabil. Jan.-Feb. 2005;26(1):87-97.
Tager-Flusberg, et al. Language disorders: autism and other pervasive developmental disorders. Pediatr Clin North Am. Jun. 2007;54(3):469-81, vi.
Thomas, et al. Defective protein folding as a basis of human disease. Trends Biochem Sci. Nov. 1995;20(11):456-9.
Torrente, et al. Focal-enhanced gastritis in regressive autism with features distinct from Crohn's and *Helicobacter pylori* gastritis. Am J Gastroenterol. Apr. 2004;99(4):598-605.
Torrente, et al. Small intestinal enteropathy with epithelial IgG and complement deposition in children with regressive autism. Mol Psychiatry. 2002;7(4):375-82, 334.
Trauner, et al. Specific cognitive deficits in young children with cystinosis: evidence for an early effect of the cystinosin gene on neural function. J Pediatr. Aug. 2007;151(2):192-6.
Uhlmann, et al. Potential viral pathogenic mechanism for new variant inflammatory bowel disease. Mol Pathol. Apr. 2002;55(2):84-90.
Unis, et al. A randomized, double-blind, placebo-controlled trial of porcine versus synthetic secretin for reducing symptoms of autism. J Am Acad Child Adolesc Psychiatry. Nov. 2002;41(11):1315-21.
Valicenti-McDermott, et al. Frequency of gastrointestinal symptoms in children with autistic spectrum disorders and association with family history of autoimmune disease. J Dev Behav Pediatr. Apr. 2006;27(2 Suppl):S128-36.
Vargas, et al. Neuroglial activation and neuroinflammation in the brain of patients with autism. Ann Neurol. Jan. 2005;57(1):67-81.
Vellard. The enzyme as drug: application of enzymes as pharmaceuticals. Curr Opin Biotechnol. Aug. 2003;14(4):444-50.
Vilanova, et al. Preparative isolation of the two forms of pig pancreatic pro-(carboxypeptidase A) and their monomeric carboxypeptidases A. Biochem J. Aug. 1, 1985;229(3):605-9.
Vojdani, et al. Antibodies against CNS antigens in autism: Possible cross-reaction with dietary proteins and infectious agent antigens. Neuropsychiatric Disorders and Infection. 2004; 19:171-186.
Vojdani, et al. Heat shock protein and gliadin peptide promote development of peptidase antibodies in children with autism and patients with autoimmune disease. Clin. Diagn Lab Immunol. May 2004;11(3):515-24.
Vojdani, et al. Immune response to dietary proteins, gliadin and cerebellar peptides in children with autism. Nutr Neurosci. Jun. 2004;7(3):151-61.
Volkmar, et al. Practice parameters for the assessment and treatment of children, adolescents, and adults with autism and other pervasive developmental disorders. American Academy of Child and Adolescent Psychiatry Working Group on Quality Issues. J Am Acad Child Adolesc Psychiatry. (Part 1) Dec. 1999;38(12 Suppl):32S-54S.
Volkmar, et al. Practice Parameters for the Assessment and Treatment of Children, Adolescents, and Adults with Autism and other Pervasive Developmental Disorders. American Academy of Child and Adolescent Psychiatry. J Am Acad Child Adolesc Psychiatry. (Part 2) Dec. 1999;38(12):1611-6.
Wakefield, et al. Enterocolitis in children with developmental disorders. Am J Gastroenterol. Sep. 2000;95(9):2285-95.
Wakefield, et al. Ileal-lymphoid-nodular hyperplasia, non-specific colitis, and pervasive developmental disorder in children. Lancet. Feb. 28, 1998;351(9103):637-41.
Wakefield, et al. Review article: the concept of entero-colonic encephalopathy, autism and opioid receptor ligands. Aliment Pharmacol Ther. Apr. 2002;16(4):663-74.
Wakefield, et al. The significance of ileo-colonic lymphoid nodular hyperplasia in children with autistic spectrum disorder. Eur J Gastroenterol Hepatol. Aug. 2005;17(8):827-36.
Wakefield. Autistic enterocolitis: is it a histopathological entity? Histopathology. 2006; 1-5.
Wakefield. The gut-brain axis in childhood developmental disorders. J Pediatr Gastroenterol Nutr. May-Jun. 2002;34 Suppl 1:S14-7.
Walsh, et al. Heat shock and the role of the HSPs during neural plate induction in early mammalian CNS and brain development. Cell Mol Life Sci. Feb. 1997;53(2):198-211.
Wang, et al. Activation of Ras/Erk pathway by a novel MET-interacting protein RanBPM. J Biol Chem. Sep. 27, 2002;277(39):36216-22.
Weintraub, et al. Morphometric studies of pancreatic acinar granule formation in NCTR-Balb/c mice. J Cell Sci. May 1992;102 ( Pt 1):141-7.
Welch, et al. Brain effects of chronic IBD in areas abnormal in autism and treatment by single neuropeptides secretin and oxytocin. J Mol Neurosci. 2004;25(3):259-74.
Whitehouse. Fact Sheet: Combating Autism Act of 2006. www.whitehouse.gov. Dec. 19, 2006.
Williams, et al. Eating habits of children with autism. Pediatr Nurs. May-Jun. 2000;26(3):259-64.

(56) References Cited

OTHER PUBLICATIONS

Yahoo!.com. Who is affected by Parkinson's disease. Yahoo! Health. Jul. 14, 2008.
Yazbak. Autism in the United States: a perspective. Journal of American Physicians and Surgeons. 2003;8:103-107.
Youngberg, et al. Comparison of gastrointestinal pH in cystic fibrosis and healthy subjects. Dig Dis Sci. May 1987;32(5):472-80.
Yuan, et al.. Freeze-Thaw Stability of Three Waxy Maize Starch Pastes Measured by Centrifugation and Calorimetry. Cereal Chem. 1998; 75(4):571-573.
Zeiner, et al. Mammalian protein RAP46: an interaction partner and modulator of 70 kDa heat shock proteins. EMBO J. Sep. 15, 1997;16(18):5483-90.
U.S. Appl. No. 13/144,286, filed Jul. 12, 2011, Fallon et al.
U.S. Appl. No. 13/144,290, filed Jul. 12, 2011, Fallon et al.
U.S. Appl. No. 13/204,881, filed Aug. 8, 2011, Fallon et al.
U.S. Appl. No. 13/208,963, filed Aug. 12, 2011, Fallon.
Liyanage, et al. Bioavailability of iron from micro-encapsulated iron sprinkle supplement. Food and Nutrition bulletin. 2002; 23(3):133-137.
Notice of Allowance dated Sep. 20, 2011 for U.S. Appl. No. 12/283,090.
Office action dated Oct. 19, 2011 for U.S. Appl. No. 12/386,051.
Final Office Action dated Nov. 8, 2011 for U.S. Appl. No. 12/054,343.
Final Office Action dated Nov. 8, 2011 for U.S. Appl. No. 12/786,739.
TheFreeDictionary. Term Sprinkles Www.thefreedictionary.com. Accessed Nov. 2, 2011. 1 page.
U.S. Appl. No. 13/481,087, filed May 25, 2012, Fallon.
Dajcs, et al. Lysostaphin is effective in treating methicillin-resistant *Staphylococcus aureus* endophthalmitis in the rabbit. Curr Eye Res. Jun. 2001;22(6):451-7.
Kokai-Kun, et al. Lysostaphin as a treatment for systemic *Staphylococcus aureus* infection in a mouse model. J Antimicrob Chemother. Nov. 2007;60(5):1051-9. Epub. Sep. 10, 2007.
Office action dated Jun. 13, 2012 for U.S. Appl. No. 12/493,122.
U.S. Appl. No. 13/193,346, filed Jul. 28, 2011, Fallon.
U.S. Appl. No. 13/313,629, filed Dec. 7, 2011, Fallon.
U.S. Appl. No. 13/313,708, filed Dec. 7, 2011, Fallon.
U.S. Appl. No. 13/407,408, filed Feb. 28, 2012, Fallon et al.
U.S. Appl. No. 13/448,061, filed Apr. 16, 2012, Fallon.
U.S. Appl. No. 13/502,989, filed Apr. 19, 2012, Heil et al.
U.S. Appl. No. 13/503,844, filed Apr. 24, 2012, Fallon et al.
Elkashef, et al. Biological markers of cocaine addiction: implications for medications development. Addict Biol. Jun. 2003;8(2):123-39.
Fallon. Could one of the most widely prescribed antibiotics amoxicillin/clavulanate "augmentin" be a risk factor for autism? Med Hypotheses. 2005;64(2):312-5.
Final Office Action dated Jan. 3, 2012 for U.S. Appl. No. 10/681,018.
Final Office Action dated Jan. 26, 2012 for U.S. Appl. No. 12/487,864.
Horvath, et al. Autism and gastrointestinal symptoms. Curr Gastroenterol Rep. Jun. 2002;4(3):251-8.
Isaksson, et al. Pain reduction by an oral pancreatic enzyme preparation in chronic pancreatitis. Digestive Dis. Sci. 1983; 28(2):97-102.
Jenkins, et al. Management of gastroenteritis. Archives of Disease in Childhood. 1990; 65:939-941.
Lashkari, et al. Williams-Beuren syndrome: An update and review for the primary physician. Clinical Pediatrics. 1999; 38(4):189-208.
Martin, et al. A rapid and sensitive spectrophotometric method for the assay of chymotrypsin. Biol Chem. Feb. 1959;234(2):294-8.
Meyer-Lindenberg, et al. Neural mechanisms in Williams syndrome: a unique window to genetic influences on cognition and behavior. Nat. Rev. Neurosci. 2006; 7(5):380-93.
Notice of Allowance dated Feb. 17, 2012 for U.S. Appl. No. 10/681,018.
Notice of Allowance dated Mar. 20, 2012 for U.S. Appl. No. 12/487,864.
Office Action dated Feb. 1, 2012 for U.S. Appl. No. 12/493,122.

Office Action dated Mar. 5, 2012 for U.S. Appl. No. 12/535,676.
Office Action dated Mar. 19, 2012 for U.S. Appl. No. 13/204,881.
Office Action dated Mar. 23, 2012 for U.S. Appl. No. 13/271,783.
Office Action dated Apr. 5, 2012 for U.S. Appl. No. 11/555,697.
Office Action dated Apr. 9, 2012 for U.S. Appl. No. 13/208,963.
Office action dated Dec. 15, 2011 for U.S. Appl. No. 12/493,147.
Peters, et al. Treatment of alcoholic polyneuropathy with vitamin B complex: a randomised controlled trial. Alcohol Alcohol. Nov.-Dec. 2006;41(6):636-42. Epub Aug. 21, 2006.
Schumann. Medical, nutritional and technological properties of lactulose. An update. Eur J Nutr. Nov. 2002;41 Suppl 1:117-25.
Sillanaukee, et al. Improved diagnostic classification of alcohol abusers by combining carbohydrate-deficient transferrin and gamma-glutamyltransferase. Clin Chem. Apr. 2001;47(4):681-5.
Tran, et al. Treatment of complex regional pain syndrome: a review of the evidence. Can J Anaesth. Feb. 2010;57(2):149-66.
U.S. Appl. No. 13/705,763, filed Dec. 5, 2012, Fallon et al.
U.S. Appl. No. 13/562,999, filed Jul. 31, 2012, Fallon.
Bowers. Endocrine secretions of the pancreas. Jul. 5, 2006. Accessed online at www.vivo.colostate.edu/hbooks/pathphys/digestion/pancreas/exocrine.html.
Dupiereux, et al. Creutzfeldt-jakob, Parkinson, lewy body dementia and Alzheimer diseases: from diagnosis to therapy. Cent Nery Syst Agents Med Chem. Mar. 2009;9(1):2-11.
Notice of allowance dated Jul. 3, 2012 for U.S. Appl. No. 13/271,783.
Office action dated Jun. 27, 2012 for U.S. Appl. No. 12/493,147.
Office action dated Jul. 11, 2012 for U.S. Appl. No. 12/573,353.
Office action dated Aug. 13, 2012 for U.S. Appl. No. 13/208,963.
Office action dated Sep. 13, 2012 for U.S. Appl. No. 13/481,087.
Office action dated Oct. 10, 2012 for U.S. Appl. No. 13/201,881.
Office action dated Oct. 25, 2012 for U.S. Appl. No. 13/144,286.
Office action dated Oct. 25, 2012 for U.S. Appl. No. 13/144,290.
Wisniewski, et al. Therapeutic approaches for prion and Alzheimer's diseases. FEBS J. Aug. 2007;274(15):3784-98. Epub Jul. 6, 2007.
Amendment dated Jul. 2, 2008 in Reply to Notice of Non-Compliant Amendment dated Jun. 2, 2008 for U.S. Appl. No. 12/046,252.
Amendment dated Aug. 19, 2009 in Reply to Notice Non-Compliant Amendment dated Jun. 19, 2009 for U.S. Appl. No. 11/232,180.
Amendment dated Aug. 21, 2008 in Reply to Office Action dated Apr. 21, 2008 for U.S. Appl. No. 11/232,180.
Amendment dated Aug. 28, 2008 in Reply to Office Action dated Mar. 28, 2008 for U.S. Appl. No. 11/555,697.
Amendment dated Sep. 24, 2007 in Reply to Restriction Requirement dated Jun. 22, 2007 for U.S. Appl. No. 11/213,255.
Amendment dated Sep. 25, 2008 in Reply to Final Office Action dated Jun. 25, 2008 for U.S. Appl. No. 11/213,255.
Amendment in Response dated May 23, 2003 to Restriction Requirement dated Apr. 23, 2003 for U.S. Appl. No. 09/990,909.
Axelrod. Secretin Treatment for Gastrointestinal Dysmobility in Patients with Familial Dysautonomia. New York University School of Medicine, Grant Recipient awards, Mar.-May 2000. www.med.nyu.edu/ogars/awards/awards2000/page2.html.
Azilect et al. "Correlation between protein intake and daily levodopa dosage," Obtained from the internet May 2, 2007, http://www.azilect.eu/media/cnsnews/showitem.aspx?i=d1c603e4-3c61-4aa1-a376-6e519a5a0f80.
Barlow. A comparison of the blood pressure, kidney volume and the pancreatic secretory response following the vein administration of various secretin preparations. Am J Phys. 1927;81:182-188.
Belmonte et al. Fragile X syndrome and autism at the intersection of genetic and neural networks. Nat Neurosci. Oct. 2006; 9(10):1221-5 (abstract only).
Hoshiko et al. The effect of the gastrointestinal hormones on colonic muscosal blood flow. Acta Medica Nagasakiensia. 1994; 39(4):125-130.
International search report and written opinion dated Jan. 18, 2011 for PCT/US2010/057341.
International search report and written opinion dated Feb. 15, 2011 for PCT/US2010/053484.
International search report and written opinion dated Mar. 2, 2010 for PCT/US2010/020253.
International search report and written opinion dated Jun. 9, 2010 for PCT/US2010/030895.

(56) References Cited

OTHER PUBLICATIONS

International search report and written opinion dated Sep. 25, 2009 for PCT/US2009/049374.
International search report and written opnion dated Mar. 5, 2010 for PCT/US2010/020259.
International search report dated Mar. 11, 2002 for PCT/US2001/25343.
International search report dated Jun. 20, 2001 for PCT/US2000/34000.
Kaspar et al. New photometric assay for chymotrypsin in stool. Clinical Chemistry. 1984; 30(11):1753-1757.
Layer et al. Pancreatin enzyme replacement therapy. Current Gastroenterology Reports. 2001; 1:101-108.
Lieberman. Pharmaceutical Dosage Forms. vol. 2: Disperse Systems. New York Marcel Dekker, Inc. 1996; 243-258.
Lipase 30, Technical Data sheet, 1 page, Scientific Protein Laboratories LLC Jun. 13, 2005.
Macready. Parkinson's Diseasne Treatment: what you should know. Retrieved from the internet on Sep. 15, 2009, http://www.everydayhealth.com/parkinsons-disease-treatment-overview.aspx.
Marczewska et al. Protein intake in parkinsonian using the EPIC food frequency questionnaire. Mov Diord. Aug. 2006; 21(8):1229-1231.
Marlicz et al. Determination of chymotrypsin in the stool in the diagnosis of chronic pancreatitis. Wiadomosci lekarskie. 1988; 41(11):704-707. (Not in English).
Marsh. Neuropsychiatric aspects of parkinson's disease. Psychosomatics. 2000; 41(1):15-23.
Mayo Clinic Staff. Autism. Retrieved from internet Mar. 10, 2008, http://www.mayoclinic.com/health/autism/DS00348DSECTION=2.
Mayo Clinic Staff. Bipolar disorder. Jan. 4, 2008, http://www.mayoclinic.com/health/bipolardisorder/DS00356/DSECTION=symptoms.
Mayo Clinic Staff. Obsessive-compulsive disorder. Dec. 21, 2006. http://www.preferredalternatives.org/lat/WellnessLibrary/anxiety&PanicDisorders/Obsessive-CompulsiveDisorder/Obsessive-CompulsiveDisorder-Mayoclinic.pdf.
Mayo Clinic Staff. Oppositional defiant disorder. Dec. 19, 2007, http://www.mayoclinic.com/health/oppositional-defiant-disorder/DS00630/DSECTION=symptoms.
Medsafe. Data sheet for alpha-lactose, Jul. 21, 1999, http://www.medsafe.govt.nz/Profs/Datasheet/a/Alphalactulosesyrup.htm.
Merck. Autism, Merck manual online medical library home addition, retrieved from the internet Mar. 10, 2008, http://www.mercl.com/mmhge/sec23/ch286/ch286b.html.
MeSH browser, "Child Development Disorders, Pervasive," and "Attention Deficit and Disruptive Behavior Disorders," National Library of medicine. 2001; http://www.nlm.nih.gov/mesh/2002/Mbrowser.html.
Michell et al. Biomarkers and parkinson's disease. Brain. 2004; 127(8):1693-1705.
Office action dated Dec. 6, 2012 for U.S. Appl. No. 13/002,136.
Walsh, et al. Reduced violent behavior following chemical therapy. Physiology and behavior. 2004; 82:835-839.

\* cited by examiner

| | Day After Diagnosis | Protein Urine Level | Fecal Chymotrypsin Level | BP Systolic | BP Diastolic |
|---|---|---|---|---|---|
| Subject 1 | 2 | 4 | 2.2 | 155 | 96 |
| | 4 | 2 | 3 | 130 | 82 |
| | 7 | 0 | 3 | 128 | 78 |
| | 10 | 0 | 6 | 118 | 76 |
| | 15 | 0 | 6.4 | 112 | 76 |
| | 20 | 0 | 6.8 | 114 | 74 |
| | 30 | 0 | 6 | 118 | 72 |
| Subject 2 | 2 | 3 | 4.4 | 168 | 98 |
| | 4 | 3 | 4 | 140 | 86 |
| | 8 | 1 | 7 | 137 | 82 |
| | 12 | 0 | 6.4 | 130 | 78 |
| | 17 | 0 | 8 | 120 | 72 |
| | 22 | 0 | 7.4 | 118 | 70 |
| | 31 | 0 | 7 | 115 | 72 |
| Subject 3 | 2 | 3 | 3.8 | 178 | 120 |
| | 5 | 0 | 6 | 148 | 112 |
| | 7 | 0 | 5.2 | 130 | 100 |
| | 10 | 0 | 7.4 | 122 | 78 |
| | 20 | 0 | 8.8 | 114 | 77 |
| | 35 | 0 | 4.8 | 110 | 78 |
| Subject 4 | 2 | 4 | 0.4 | 155 | 98 |
| | 4 | 3 | 3 | 130 | 90 |
| | 7 | 3 | 4.4 | 124 | 88 |
| | 10 | 3 | 3.8 | 116 | 92 |
| | 16 | 0 | 5.2 | 118 | 82 |
| | 22 | 1 | 6 | 110 | 77 |
| | 31 | 0 | 6.6 | 112 | 77 |
| Subject 5 | 2 | 3 | 6.6 | 176 | 88 |
| | 4 | 3 | 8 | 160 | 82 |
| | 7 | 0 | 8 | 140 | 74 |
| | 10 | 0 | 8.8 | 122 | 72 |
| | 15 | 0 | 6.6 | 120 | 68 |
| | 23 | 0 | 7 | 110 | 66 |
| | 31 | 0 | 8.4 | 100 | 68 |
| Subject 6 | 3 | 4 | 6.6 | 145 | 96 |
| | 5 | 3 | 4.4 | 120 | 82 |
| | 7 | 3 | 8 | 116 | 72 |
| | 12 | 2 | 9.2 | 100 | 74 |
| | 15 | 2 | 8.4 | 108 | 70 |
| | 20 | 0 | 7 | 112 | 72 |
| | 30 | 0 | 7.4 | 110 | 74 |

Figure 1

Figure 4
Measurement of Fecal Chymotrypsin Levels in Preeclamptic Women

| WEEK | 12 | 14 | 16 | 18 | 20 | 22 | 24 | 26 | 28 | 30 | 32 | 34 | 36 | 38 | 40 |
|---|---|---|---|---|---|---|---|---|---|---|---|---|---|---|---|
| Subject | | | | | | | | | | | | | | | |
| 1 | 16.4 | 13 | 14.4 | 15 | 17.4 | 14.4 | 15 | 16.2 | 15.2 | 12.6 | 17.6 | 16 | 16.6 | 17.2 | 16.6 |
| 2 | 26.6 | 24.4 | 22 | 26.8 | 27 | 26.4 | 26.2 | 29 | 27.4 | 26.2 | 29.4 | 23.6 | 27.4 | 26.4 | 28 |
| 3 | 30.2 | 31 | 27.8 | 29 | 28.8 | 30.4 | 29.2 | 28.6 | 29.4 | 27.4 | 26.4 | 29 | 27.6 | 25.4 | 26 |
| 4 | 18 | 19.2 | 14 | 20.2 | 18.8 | 16.8 | 18.4 | 19.6 | 15.6 | 15 | 16.8 | 17 | 15.8 | 16.6 | 17 |
| 5 | 13.4 | 12.8 | 17.4 | 16 | 15 | 15.2 | 16 | 14.8 | 16.2 | 17 | 14.4 | 16 | 13 | 14.4 | 12 |
| 6 | 19 | 17.6 | 18.8 | 18.2 | 19.4 | 18.2 | 18.4 | 19.8 | 20.2 | 6.4 | 5.8 | 3.6 | 3.2 | 4.4 | 3.8 |
| 7 | 30 | 32.6 | 28.8 | 26.6 | 26.4 | 31 | 27.8 | 29.4 | 30.8 | 25.6 | 30 | 26.4 | 30 | 28.4 | 30.8 |
| 8 | 14.2 | 13 | 14.8 | 15.2 | 15 | 17 | 14.8 | 15.6 | 17.4 | 18.8 | 22 | 21.8 | 17.6 | 18.8 | 19 |
| 9 | 19.8 | 24.2 | 22 | 25.4 | 21 | 22.8 | 25.4 | 27.4 | 22 | 25.8 | 23.2 | 19.8 | 20.6 | 26.6 | 24 |
| 10 | 13.2 | 14 | 15.8 | 14.4 | 17 | 15.4 | 13.8 | 12 | 15 | 17.2 | 16 | 16 | 17 | 16.6 | 17 |
| 11 | 22 | 23.2 | 21 | 26 | 26.4 | 19 | 18.8 | 21 | 25.4 | 19 | 24.4 | 18.8 | 22 | 17.8 | 20.2 |
| 12 | 35.6 | 34 | 36 | 30 | 19.8 | 26.6 | 29 | 28.8 | 30 | 31.4 | 28.8 | 19.8 | 28.8 | 31 | 33.45 |
| 13 | 17.8 | 19 | 18.4 | 20.6 | 22 | 21.6 | 18.8 | 19 | 19.8 | 22.8 | 21 | 23.8 | 22 | 20.6 | 21 |
| 14 | 20.8 | 26 | 25.4 | 22 | 20.4 | 19.8 | 22 | 25.2 | 26.4 | 23.8 | 20.6 | 22.2 | 19.8 | 17.6 | 20 |
| 15 | 17.6 | 22 | 18.4 | 22.4 | 23.6 | 19.2 | 24 | 22.6 | 22.8 | 20 | 18 | 19.4 | 23.2 | 18.8 | 23 |
| 16 | 15.6 | 14 | 16.2 | 15.2 | 17 | 16.4 | 18.2 | 16.8 | 16.4 | 19 | 16.2 | 17.4 | 18.8 | 17.2 | 20 |
| 17 | 33 | 29.4 | 31.4 | 30.8 | 29.4 | 28.8 | 29.2 | 30.2 | 33 | 31.6 | 29.6 | 28.4 | 26 | 26.6 | 25 |

COMPOSITIONS AND USE THEREOF FOR TREATING SYMPTOMS OF PREECLAMPSIA

FIELD OF THE INVENTION

The invention relates to a treatment for pregnancy induced hypertension, preeclampsia, eclampsia, toxemia and related disorders of pregnancy, and more particularly, to the use of digestive/pancreatic enzymes in the treatment of pregnancy induced hypertension, preeclampsia, eclampsia and toxemia that may occur during pregnancy.

BACKGROUND OF THE INVENTION

Every year thousands of women suffer from pregnancy induced hypertension. While blood pressure during pregnancy is generally lower than in the non-pregnant state, some pregnant women will develop hypertension. Hypertension during pregnancy can have a significant impact on the mother and the fetus, including, but not limited to stroke or other cardiovascular complications. It is estimated that 7 out of every 100 pregnant women will develop toxemia/eclampsia and/or pre-eclampsia of which hypertension is the main presenting symptom. Mild toxemia, also known as preeclampsia is monitored closely and usually causes few problems for the mother or child. Of note, toxemia, and eclampsia are often used interchangeably to refer to the same condition, and will be used interchangeably throughout the application.

There is no known cause for toxemia. What is known is that toxemia starts to develop as the placenta begins to develop, although the condition may not be detected until the latter part of pregnancy. Most cases of toxemia happen with first pregnancies. Second and subsequent pregnancies are at lower risk, unless the woman is with a new partner. Since there is no known cause of toxemia, there is no way to determine if a woman is at risk for the condition before she gets pregnant.

Preeclampsia causes hypertension and proteinuria, manifesting most often after the twentieth week of pregnancy. In the past, edema was considered a diagnostic criterion. Recently, however, it has been eliminated as a requirement for diagnosis. Preeclampsia causes vasospasm, a condition in which your blood vessels squeeze and then relax almost like a muscle spasm. This causes the smooth lining of the blood vessels to become damaged and rough. Once this damage occurs, the body will send out cells to repair the damage. The cells that arrive first are platelets. As platelets and other blood products try to repair the damage, they form little clots along the blood vessel wall causing the blood vessel to become even more narrow and further decreasing blood flow to the organs. The body continually makes new platelets; however, there is a limited supply of platelets in the body at any one time. Once they have become depleted, spontaneous bleeding can occur.

Other cells passing by the damaged lining of the blood vessels break open, often spilling their toxic contents. These toxic waste products cause high blood pressure and even more damage to other organs. Vasospasm and the miniature blood clots cause further damage by decreasing blood flow and thus decreasing the oxygen supply to vital organs such as the brain, kidneys, and liver.

The term preeclampsia refers to the disease state before a seizure. Once a woman has had a seizure with this disease, it then becomes eclampsia. Eclampsia includes hypertension and proteinuria. Preeclampsia may be classified as mild or severe. Severe preeclampsia is characterized by (1) a systolic blood pressure in a known normotensive woman greater than 140-160 mm Hg or diastolic blood pressure greater than 90-110 mm Hg on 2 occasions at least 6 hours apart in a woman on bed rest and (2) the presence of significant proteinuria. Proteinuria concentration associated with preeclampsia are in the 300 mg/24 hour urine range. Marked proteinuria is defined as 5 g or more of protein in a 24-hour urine collection.

Severe preeclampsia, at times, may be associated with oliguria, cerebral or visual disturbances, pulmonary edema or cyanosis, epigastric or right upper quadrant abdominal pain, impaired liver function, thrombocytopenia, or intrauterine growth restriction. In mild preeclampsia, hypertension and proteinuria are present, but not to these extreme levels, and the patient has no evidence of other organ dysfunction. As preeclapmsia develops into eclampsia/toxemia, oliguria and other symptoms may be present. Many of the health problems associated with eclampsia/toxemia may be very dangerous to the mother and the child, and can result in severe morbidity and potentially mortality for the mother and/or the child. Toxemia may cause liver and/or kidney damage or failure. It may cause problems with eyesight and, if left untreated for too long, may cause the maternal patient to go into seizures. These seizures can lead to coma and even death. Often, the progression of these symptoms can not be stopped and full blown toxemia occurs, including kidney failure.

The etiology of preeclampsia is still unknown. Many areas have been explored including: the examination of the renin-angiotensin system, selective hormonal examination, including epinephrine, norepinephrine, and vasopressin. Further examination has included endothelin and prostaglandins, all without conclusion or an effective treatment for preeclampsia and the potential resultant eclampsia/toxemia.

Since placental delivery reverses the symptoms of preeclampsia, it suggests that the placenta may have a central role in the condition. Additionally, women with increased placental tissue for gestational age, those with hydatiform moles and/or twin or multiple pregnancies, have an increased prevalence of preeclampsia. This, therefore, leads one to consider the possibility that substances, such as human chorionic gonadotropin, which is high in a hydatiform mole, may be involved. This link between the placenta and the development of preeclampsia is key.

As the fertilized ovum begins to divide, it is known as a morula at the sixteen cell stage. As the morula enters the uterine cavity from the fallopian tube, it does not implant until day seven of gestation at which time it is termed a blastocyst. The trophoblastic cells of the blastocyst erode the uterine lining to form large pockets known as lacunae. The trophoblast now forms a divide in the cellular portion and the syncytial portion. The outside covering of the syncytial portion is known as the chorion. The chorion secretes human chorionic gonadotropin which prevents immune attack from the mother, and helps to maintain the corpus luteum of pregnancy until the maternal/fetal exchange can take place through the placenta. This is the beginning of the formation of the placenta.

The cellular trophoblast, once it begins to proliferate without proper changeover to syncytial trophoblastic activity, may cause possible syncytial demise, thus reducing the amount of steroid hormone produced, and also reducing the possibility that the placenta will form correctly. The syncytial trophoblast further proliferates to form a highly specialized trophoblast, known as an extravillous trophoblast. The extravillous trophoblast bores through the endometrium, extending to the decidua and myometrium of the uterus. These extravillous trophoblasts continue their invasion into the spiral arterioles of the uterus and replace the endothelial and muscular linings of the uterine arterioles, leading to vasodilation of the uterine vasculature. This change ensures a continued low resistance system, which potentiates maternal blood flow to the intervillous space and maintains adequate perfusion of the developing fetus.

The mechanism by which the cellular trophoblast is reduced in its proliferation such that the syncytial trophoblast can take over is the presence of proteolytic enzymes, especially that of chymotrypsin. These proteases produced by the mother, especially chymotrypsin, are able to restrain the proliferation of the cellular trophoblast and the overproduction of human chorionic gonadotropin. This mechanism was outlined by Ernest T. Krebs in 1949 (Medical Record, Vol. 162, No. 10, October 1949).

In preeclampsia, the lack of proliferation of the syncytial trophoblasts leads to a lack of extravillous trophoblasts and an improper boring into the muscular lining of the uterine arterioles. This leads to vasospasm of the arteries of the uterine endometrium and results in ischemia, anoxia, necrosis, histamine and tyramine release. With the absence of marked vasodilation and the lumen of the vessels essentially occluded, blood flow and oxygen transfer to the fetus is diminished, leading to the maternal manifestations of preeclampsia as well as the fetal manifestations of oligohydramnios and intrauterine growth restriction (IUGR).

The resultant improper placental development results in placental vascular endothelial dysfunction and a relative uteroplacental insufficiency. The vascular endothelial dysfunction results in increased permeability, hypercoagulability, and diffuse vasospasm.

The loss of protein through the kidney and excretion in the urine and the alterations in the permeability of the vascular system due to the potential endothelial dysfunction results in an increase in vascular permeability. This enhanced vascular permeability ultimately permits the proteins, especially large proteins which are large molecules, to get through the capillaries and the glomerulus of the kidney. This loss of protein creates a potential need for large amounts of protein intake during pregnancy.

With incomplete protein breakdown due to the increased permeability of the vascular system, and its ability to permit large molecules into the vascular system, the protein requirements of the body during pregnancy are even greater than in the non-pregnant state. Further, with the significant loss of protein and the resultant dearth of amino acids present in the pregnant woman, the potential exists for organ dysfunction and potential organ death.

The use of digestive enzymes can facilitate the presence of sufficient protein so as not to allow the body to go into a negative protein balance. This is highly desirable as well as necessary due to the need for proteases such that the body can facilitate formation of the placenta as well as replacement proteins which are lost by the body during the pregnancy.

In view of such findings, there is need for a method of treating those with preeclampsia such that the development of eclampsia/toxemia does not occur in pregnant women. The present invention is directed to therapeutic agents for the treatment of toxemia, preeclampsia and eclampsia and the method for preparing those agents. Further, the present invention is directed to the reduction of the formation of hydatiform moles (molar pregnancies).

More specifically, the present invention relates to stable pharmaceutical preparations containing, but not limited to, digestive/pancreatic enzymes, including, but not limited to, amylases, proteases, cellulase, papaya, papain, bromelain, lipases, chymotrypsin and hydrolases. This combination is made by, but not limited to: direct compression, microencapsulation, lipid encapsulation, wet granulation or other methods including the use of Prosolv®, microencapsulation, lipid encapsulation technology, or other suitable technology. This technology can include the use of rapid dissolution (rapid dissolve), time release or other delivery methods including oral, injection, patch or other method. Further, the delivery of the enzymes can be in the form of a tablet, sprinkles, sachet, capsules, caplets or other compressed tablet delivery, or other oral delivery method.

Further, the invention is directed toward the use of a biomarker, the presence of chymotrypsin in the maternal GI tract to determine the likelihood of developing preeclampsia, pregnancy induced hypertension, and eclampsia/toxemia.

SUMMARY OF THE INVENTION

It is a goal of the present invention to provide a therapeutic agent for the treatment of pregnancy induced hypertension, toxemia, preeclampsia and eclampsia and provide a method for preparing those agents.

Another goal of the present invention is to formulate stable pharmaceutical preparations containing, but not limited to, digestive/pancreatic enzymes including, but not limited to, amylases, proteases, cellulase, papaya, papain, bromelain, lipases, chymotrypsin; and hydrolases.

Yet another goal of the present invention is to make a combination of digestive/pancreatic enzymes is made by but not limited to: direct compression, microencapsulation, lipid encapsulation, wet granulation or other methods including the use of Prosolv®, and other known excipients and additives to accomplish microencapsulation, lipid encapsulation, direct compression, wet or dry granulation or other suitable technology.

A further goal of the present invention is to deliver the preparation by means, which can include the use of rapid dissolution (rapid dissolve), time release, or other delivery methods including oral, injection, patch, or other method. Further, the delivery of the enzymes may be in the form of a tablet, capsule, sprinkles, sachet, or other oral delivery method.

An additional goal of the invention is to demonstrate the use of fecal chymotrypsin as a prognosticative indicator of the presence of preeclampsia, eclampsia, toxemia or other disease of pregnancy, or the likelihood of a woman to develop preeclampsia, eclampsia, toxemia, or pregnancy induced hypertension.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

FIG. 1 is a table illustrating the changes in blood pressure, both diastolic and systolic, urine protein level, and fecal chymotrypsin level in pregnant women with preeclampsia that were administered pancreatic enzymes.

FIG. 4 is a chart illustrating the fecal chymotrypsin levels in seventeen pregnant women from week 12 of pregnancy through week 40 of pregnancy.

DETAILED DESCRIPTION OF THE PREFERRED EMBODIMENT

Figure 2:
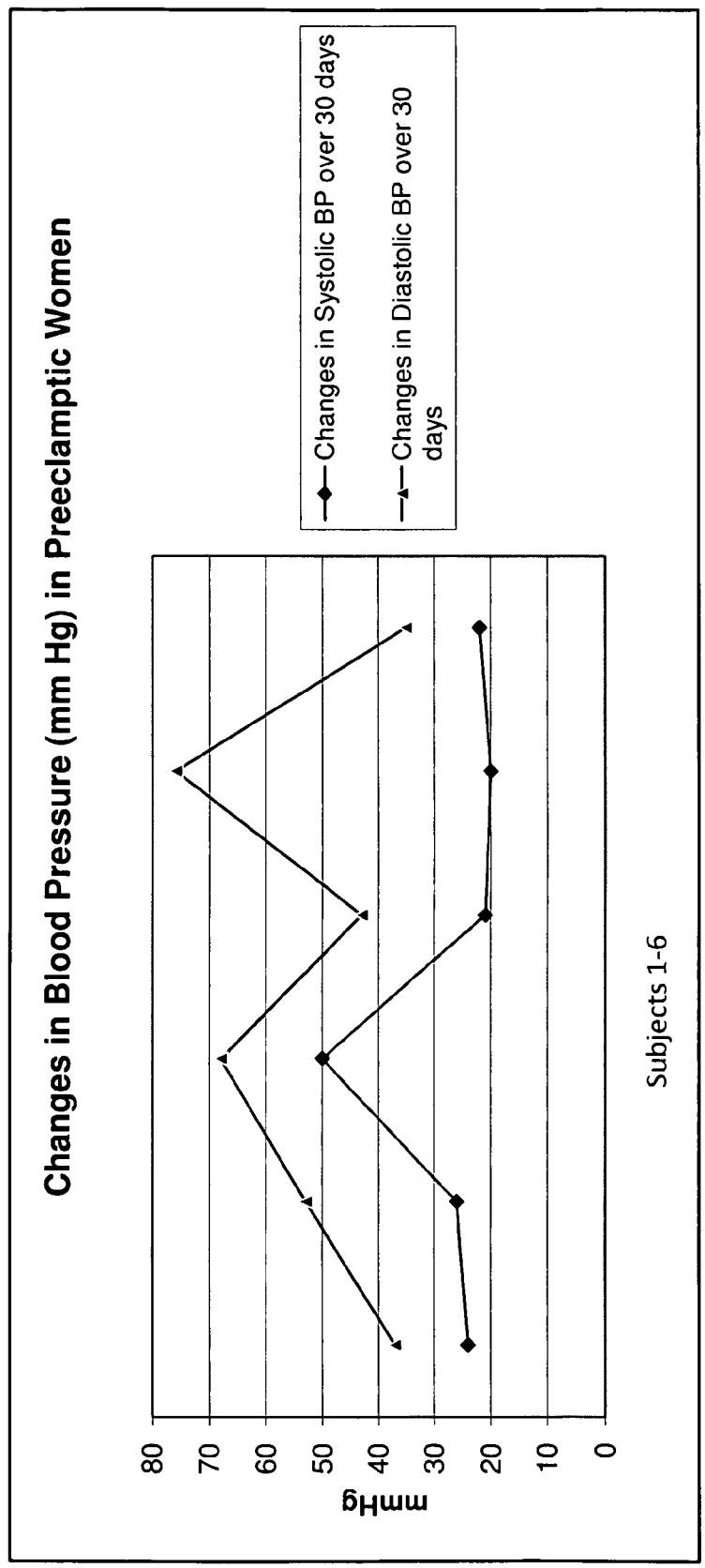
FIG. 2 is a graph illustrating the changes in blood pressure of preeclamptic women over a 30 day period after being administered pancreatic enzymes.

Since placental delivery reverses the symptoms of preeclampsia, it suggests that the placenta has a central role in the condition. Additionally, women with increased placental tissue for gestational age, or those with hydatiform moles and twin pregnancies, have an increased prevalence of preeclampsia. This leads one to consider the possibility that substances, such as human chorionic gonadotropin, which is present in an increased amount in a hydatiform mole, may be involved. This link between formation of the placenta and the development of preeclampsia is key.

The formation of the syncytial trophoblast, and its secretion of steroid hormones keeps the levels of human chorionic gonadotropin low, and thereby reduces the likelihood of developing preeclampsia. The syncytial trophoblast further proliferates to form a highly specialized trophoblast, known as an extravillous trophoblast. The extravillous trophoblast bores through the endometrium, extending to the decidua and myometrium. These extravillous trophoblasts continue their invasion into the spiral arterioles and replace the endothelial and muscular linings of the uterine arterioles, leading to vasodilation of the uterine vasculature. This change ensures a continued low resistance system, which potentiates maternal blood flow to the intervillous space and maintains adequate perfusion of the developing fetus.

The mechanism by which the cellular trophoblast is reduced in its proliferation so that the syncytial trophoblast may take over is the presence of proteolytic enzymes, especially that of chymotrypsin. The maternal proteases, especially that of chymotrypsin, are able to restrain the proliferation of the cellular trophoblast and the overproduction of human chorionic gonadotropin.

In one embodiment, a stable preparation of digestive/pancreatic enzymes is formed into a dosage formulation containing a therapeutically effective amount of a protease, an amylase, and/or a lipase. The formulation may include additional enzymes, such as pancreatin, chymotrypsin, trypsin, papain and/or papaya. Other combinations of digestive enzymes may also be used. These enzymes can be in the form of animal or plant derivatives, natural or synthetic.

The following outlines a formulary for digestive/pancreatic enzymes for preeclampsia/toxemia:
Amylase 10,000-60,000 U.S.P
Protease 10,000-70,000 U.S.P
Lipase 4,000-30,000 U.S.P
Pancreatin 2,000-6,000 U.S.P
Chymotrypsin 2-5 mg
Trypsin 60-100 mg
Papain 3,000-10,000 USP units/mg
Papaya 30-60 mg The dosage formulation may be administered by an oral preparation including, but not limited to, an encapsulated tablet, mini-tabs, microcapsule, mini-capsule, time released capsule, sprinkle or other methodology. In one embodiment, the oral preparation is encapsulated using Prosolv technology. Alternatively, the oral preparation may be encapsulated using enteric coating, lipid encapsulation, direct compression, dry granulation, wet granulation, and/or a combination of these methods.

In a study conducted by the inventor, six women diagnosed with preeclampsia in weeks 28-34 of pregnancy were examined. Each was administered pancreatic enzymes, including lipases, amylases and proteases, within two days of their diagnosis of preeclampsia for the duration of their pregnancy, while being monitored by their obstetricians. The results of the study are found in FIG. 1, which illustrates the changes in the womens' blood pressure, both diastolic and systolic, urine protein level, and fecal chymotrypsin levels.

As seen in FIG. 2, it is clear from the results that the blood pressures of the pregnant women were reduced significantly over the 30 days of administration of the pancreatic enzymes. In every case, their blood pressures returned to normal, which is usually 120/80. In some cases, the reversion to a normal blood pressure reading occurred within 15 days.

Figure 3:
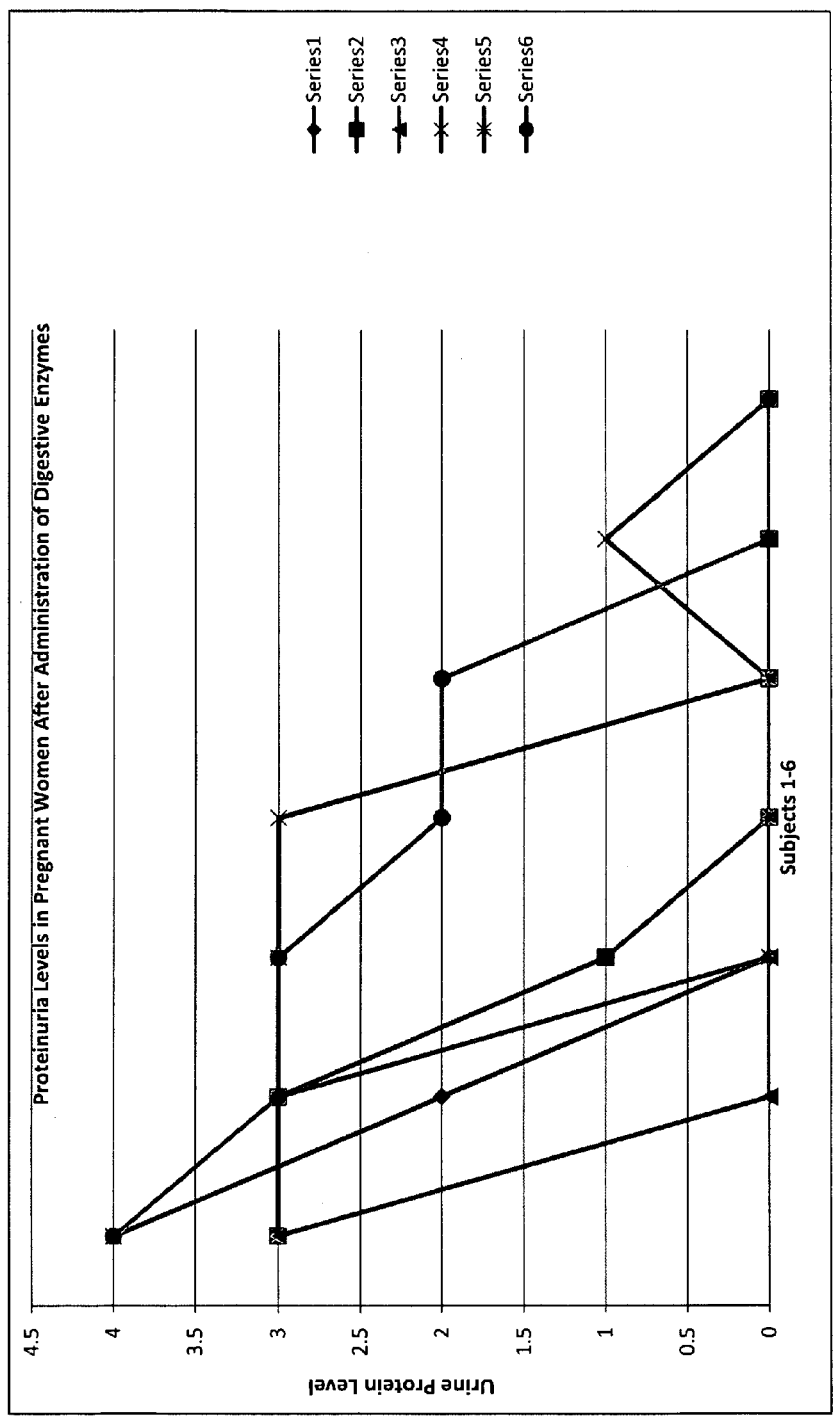
FIG. 3 is a graph illustrating the changes in urine protein level of preeclamptic women over a 30 day period after being administered pancreatic enzymes.

Further, the levels of protein in their urine also reverted to normal within 30-35 days as seen in FIG. 3. Proteinuria is diagnosed by examining the urine through a simple urinalysis. Normal urine has very small amounts of protein present. Larger amounts are usually reported as 1+ to 4+.

In another study, shown in FIG. 4, seventeen women that were pregnant for the first time (primipara) that were in their first trimester were administered a fecal chymotrypsin test every other week from week 12 to week 40 of their pregnancy. One woman, subject 6, developed preeclamptic symptoms, and her fecal chymotrypsin test became abnormal one week prior to the diagnosis of preeclampsia.

Fecal chymotrypsin is a sensitive, specific measure of proteolytic activity. Normal levels of chymotrypsin are considered be greater than 8.4 U/gram. Decreased values (less than 4.2 U/gram) suggest diminished pancreatic output (pancreatic insufficiency), hypoacidity of the stomach or cystic fibrosis. Elevated chymotrypsin values suggest rapid transit time, or less likely, a large output of chymotrypsin from the pancreas.

For the fecal chymotrypsin test, a stool sample was collected from each of the subjects. Each stool sample was analyzed using an enzymatic photospectrometry analysis to determine the level of fecal chymotrypsin in the stool. Alternatively, other methods, such as the colorimetric method, use of substrates, use of assays, and/or any other suitable method may be used to measure the fecal chymotrypsin levels. The levels of fecal chymotrypsin in the samples of the primipara pregnant women were compared to the levels of fecal chymotrypsin in pregnant women not diagnosed with preeclampsia to determine if the primipara pregnant women would benefit from the administration of digestive enzymes.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A method for treating an individual having preeclampsia characterized by hypertension, proteinuria, or a combination thereof, comprising administering a preparation of digestive enzymes comprising an amylase, a lipase, and a protease to the individual, wherein the individual having preeclampsia is treated.

2. The method of claim 1, wherein the protease comprises chymotrypsin, trypsin, papain, or a combination thereof.

3. The method of claim 1, wherein the digestive enzymes are obtained from a source comprising animal enzymes, plant enzymes, synthetic enzymes, or a combination thereof.

4. The method of claim 1, wherein the preparation of digestive enzymes is manufactured using a technology selected from the group consisting of enteric coating, lipid encapsulation, direct compression, dry granulation, wet granulation, and a combination thereof.

5. The method of claim 1, wherein the preparation of digestive enzymes is administered orally via a dosage formulation selected from the group consisting of: pills, tablets, capsules, microcapsules, mini-capsules, time released capsules, mini-tabs, sprinkles, and a combination thereof.

6. The method of claim 1, wherein the preperation of digestive enzymes comprises amylase in an amount from 10,000 to 60,000 USP units/dose.

7. The method of claim 1, wherein the preparation of digestive enzymes comprises protease in an amount from 10,000 to 70,000 USP units/dose.

8. The method of claim 1, wherein the preparation of digestive enzymes comprises lipase in an amount from 4,000 to 30,000 USP units/dose.

9. The method of claim 2, wherein the chymotrypsin is present in an amount from 2 to 5 mg.

10. The method of claim 2, wherein the papain is present in an amount from 3,000 to 10,000 USP units/dose.

11. The method of claim 2, wherein the trypsin is present in an amount from 60 to 100 mg.

12. The method of claim 1, wherein the total amount of digestive enzymes present is in an amount from about 4,000 to about 176,000 USP/dose.

\* \* \* \* \*

UNITED STATES PATENT AND TRADEMARK OFFICE
CERTIFICATE OF CORRECTION

| | | |
|---|---|---|
| PATENT NO. | : 8,658,163 B2 | Page 1 of 1 |
| APPLICATION NO. | : 12/047818 | |
| DATED | : February 25, 2014 | |
| INVENTOR(S) | : Joan M. Fallon | |

It is certified that error appears in the above-identified patent and that said Letters Patent is hereby corrected as shown below:

In the Claims

COLUMN 7, LINE 9:
In Claim 6 "wherein the preperation of" should read --wherein the preparation of--.

Signed and Sealed this
Seventh Day of July, 2015

Michelle K. Lee
*Director of the United States Patent and Trademark Office*